United States Patent
Kato et al.

(10) Patent No.: US 10,900,950 B2
(45) Date of Patent: Jan. 26, 2021

(54) APPARATUS AND ANALYTICAL EVALUATION METHODS USING MORPHOLOGICAL FEATURE PARAMETERS OF A CELL OR CELL POPULATION

(71) Applicant: National University Corporation Nagoya University, Nagoya (JP)

(72) Inventors: Ryuji Kato, Nagoya (JP); Kei Kanie, Nagoya (JP); Hiroto Sasaki, Nagoya (JP); Shun Kawai, Nagoya (JP)

(73) Assignee: National University Corporation Nagoya University, Nagoya (JP)

( * ) Notice: Subject to any disclaimer, the term of this patent is extended or adjusted under 35 U.S.C. 154(b) by 0 days.

(21) Appl. No.: 15/563,155

(22) PCT Filed: Mar. 29, 2016

(86) PCT No.: PCT/JP2016/060146
§ 371 (c)(1),
(2) Date: Sep. 29, 2017

(87) PCT Pub. No.: WO2016/158962
PCT Pub. Date: Oct. 6, 2016

(65) Prior Publication Data
US 2018/0080918 A1     Mar. 22, 2018

(30) Foreign Application Priority Data

Mar. 30, 2015 (JP) ................. 2015-070319
Mar. 30, 2015 (JP) ................. 2015-070320
Mar. 30, 2015 (JP) ................. 2015-070410

(51) Int. Cl.
| | |
|---|---|
| *G01N 33/483* | (2006.01) |
| *G01N 33/48* | (2006.01) |
| *C12Q 1/02* | (2006.01) |
| *C12M 1/34* | (2006.01) |
| *G06K 9/00* | (2006.01) |

(52) U.S. Cl.
CPC ........... *G01N 33/4833* (2013.01); *C12M 1/34* (2013.01); *C12Q 1/02* (2013.01); *G01N 33/48* (2013.01); *G01N 33/483* (2013.01); *G06K 9/0014* (2013.01)

(58) Field of Classification Search
None
See application file for complete search history.

(56) References Cited

U.S. PATENT DOCUMENTS

| | | |
|---|---|---|
| 9,567,560 B2 | 2/2017 | Honda et al. |
| 2012/0092478 A1 | 4/2012 | Honda et al. |

FOREIGN PATENT DOCUMENTS

| | | |
|---|---|---|
| JP | 2011-030494 A | 2/2011 |
| JP | 2011-229409 A | 11/2011 |
| JP | 2011-229410 A | 11/2011 |
| JP | 2011-229413 A | 11/2011 |
| JP | 2011-232051 A | 11/2011 |
| JP | 2012-175946 A | 9/2012 |
| WO | WO 2010/098105 A1 | 9/2010 |
| WO | WO 2010/098105 A1 | 8/2012 |

OTHER PUBLICATIONS

Eliceiri, Kevin W., et al. "Biological imaging software tools." Nature methods 9.7 (2012): 697.*
Supplementary European search report issued in EP Patent Application No. 16772843.5, dated Jan. 2, 2018.
Office Action issued in EP Patent Application No. 16772843.5, dated Jan. 19, 2018.
Carpenter et al., CellProfiler: image analysis software for identifying and quantifying cell phenotypes. Genome Biol. 2006;7(10):R100. Epub Oct. 31, 2006, XP021027289.
Matsuoka et al., Characterization of time-course morphological features for efficient prediction of osteogenic potential in human mesenchymal stem cells. Biotechnol Bioeng. Jul. 2014;111(7):1430-9. doi: 10.1002/bit.25189. Epub Jan. 30, 2014, XP055431564.
Matsuoka et al., Morphology-based prediction of osteogenic differentiation potential of human mesenchymal stem cells. PLoS One. 2013;8(2):e55082. doi: 10.1371/journal.pone.0055082. Epub Feb. 21, 2013, XP055431610.
Sasaki et al., Comparisons of cell culture medium using distribution of morphological features in microdevice. J Biosci Bioeng. Jan. 2016;121(1):117-123. doi: 10.1016/j.jbiosc.2015.05.011. Epub Jul. 3, 2015 XP029365560.
Sasaki et al., Image-based cell quality assessment: modeling of cell morphology and quality for clinical cell therapy. Comp. Modeling in Tissue Eng., Springer Berlin Heidelberg. 2012;207-26. doi: 10.1007/8415_2012_132. XP009502107.

(Continued)

*Primary Examiner* — G Steven Vanni
(74) *Attorney, Agent, or Firm* — Wolf, Greenfield & Sacks, P.C.

(57) ABSTRACT

The purpose of the present invention is to make it possible to efficiently generate information for cell analysis. A feature-group information generating unit generates, as feature-group information, information including values of N types of feature parameters (wherein N represents an integer having a value of 1 or more) about a morphological feature of a single cell of a plurality of cells or a morphological feature of a cell population based on data of one or more cell images included in a unit, the one or more cell images in the unit being selected from cell images capturing the cell population including the cells in accordance with a predetermined requirement. An analytical-model generating unit or an evaluation-target information acquiring unit acquires, as analyzing information for use in conducting predetermined cell analysis, information including values of M types (wherein M is an integer having a value independent of N) of parameters based on at least one of the N types of feature parameters included in the feature-group information.

5 Claims, 29 Drawing Sheets

(56) References Cited

OTHER PUBLICATIONS

Sasaki et al., Image-based focused counting of dividing cells for non-invasive monitoring of regenerative medicine products. J Biosci Bioeng. Nov. 2015;120(5):582-90. doi: 10.1016/j.jbiosc.2015.03.002. Epub Apr. 24, 2015. XP055431535.

Sasaki et al., Non-invasive quality evaluation of confluent cells by image-based orientation heterogeneity analysis. J Biosci Bioeng. Feb. 2016;121(2):227-34. doi: 10.1016/j.jbiosc.2015.06.012. Epub Jul. 13, 2015. XP029378601.

Sasaki et al., Orientation based segmentation for phase-contrast microscopic image of confluent cell. Conf Proc IEEE Eng Med Biol Soc. 2013;2013:3323-6. doi: 10.1109/EMBC.2013.6610252. XP032489778.

Suga et al., Development of a Monitoring Method for Nonlabeled Human Pluripotent Stem Cell Growth by Time-Lapse Image Analysis. Stem Cells Transl Med. Jul. 2015;4(7):720-30. doi: 10.5966/sctm.2014-0242. Epub May 13, 2015. XP055431659.

Tokunaga et al., Computational image analysis of colony and nuclear morphology to evaluate human induced pluripotent stem cells. Sci Rep. Nov. 11, 2014;4:6996. doi: 10.1038/srep06996, XP055208875.

International Search Report and Written Opinion dated Jun. 28, 2016 for Application No. PCT/JP2016/060146.

Sasaki, H., et al., Label-free morphology-based prediction of multiple differentiation potentials of human mesenchymal stem cells for early evaluation of intact cells. PLoS One. Apr. 4, 2014;9(4):e93952. doi: 10.1371/journal.pone.0093952. eCollection 2014.

\* cited by examiner

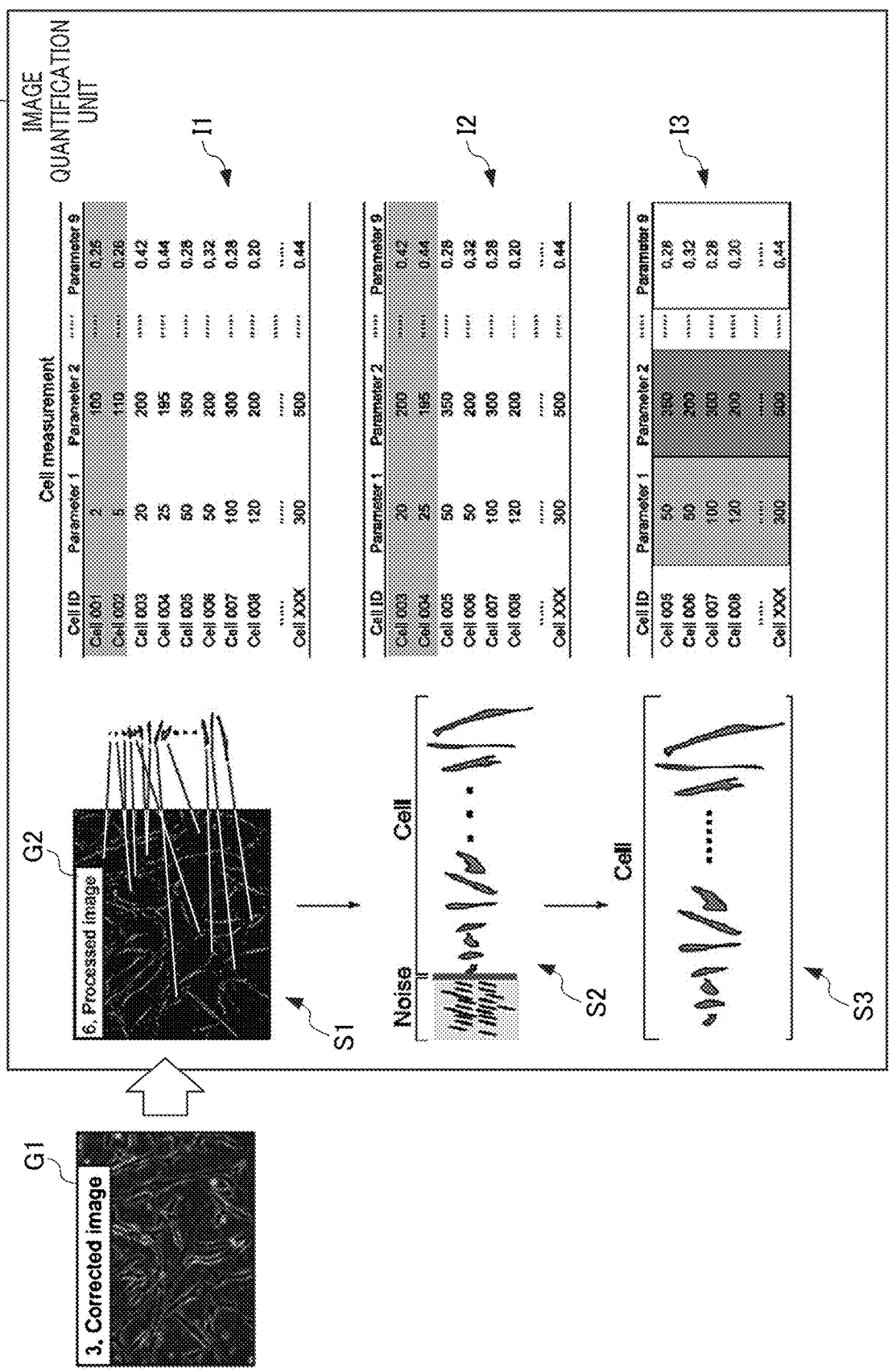

FIG. 5

| No. | Original parameter | Example | Description |
|---|---|---|---|
| 1 | Total area | | Area of object including any holes present, regardless of hole-filling. |
| * | Area | | Area of the object without hole area. |
| * | Perimeter | | Perimeter of the object measuring from the mid-points of each pixels around the border. |
| * | Length | | Length of the longest chord through the object. |
| 2 | Breadth | | Capliper width of the object perpendicular to the longest chord. |
| 3 | Inner radius | | Distance from the centroid to the nearest point along the edge of the object. |

| No. | Composite parameter | Formula | Explanation |
|---|---|---|---|
| 4 | Elliptical form factor | Elliptical form factor = $\dfrac{\text{Length}}{\text{Breadth}}$ | The elliptical from factor, the ratio of the object's breadth to its length. |
| 5 | Fiber breadth | Fiber breadth = $1/4 \times (P + \sqrt{P^2 - 16 \times A})$ (where P = Perimeter, A = Area) | Width of the object assuming that it is a fiber. |
| 6 | Fiber length | Fiber length = $1/4 \times (P - \sqrt{P^2 - 16 \times A})$ (where P = Perimeter, A = Area) | Length of the object assuming that it is a fiber. |
| 7 | Shape factor | Shape factor = $\dfrac{4\pi \times \text{Area}}{\text{Perimeter}^2}$ | Value from 0 to 1, representing how closely the object represents a circle. (circle = 1) |

FIG. 7

| Cell | CA | CB | CC | CD |
|---|---|---|---|---|
| Normal Area AVE 01pas | | 677 | | 713 |
| Normal Area AVE 02pas | | 993 | | 723 |
| Normal Area AVE 03pas | | 1010 | | 706 |
| Normal Area AVE 04pas | | 1157 | | 652 |
| Normal Area AVE 05pas | | 1050 | | 667 |
| Normal Area AVE 06pas | | 973 | | |
| Normal Area AVE 07pas | 648 | 828 | | |
| Normal Area AVE 08pas | 717 | 756 | | |
| Normal Area AVE 09pas | 785 | 766 | | |
| Normal Area AVE 10pas | 829 | 787 | | |
| Normal Area SD 01pas | | 292 | 543 | 398 |
| Normal Area SD 02pas | | 555 | | 385 |
| Normal Area SD 03pas | | 563 | | 371 |
| Normal Area SD 04pas | | 541 | | 360 |
| Normal Area SD 05pas | | 551 | | 369 |
| Normal Area SD 06pas | | 575 | | 339 |
| Normal Area SD 07pas | | 528 | | |
| Normal Area SD 08pas | 303 | 524 | | 351 |
| Normal Area SD 09pas | 406 | 571 | | 363 |
| Normal Area SD 10pas | 500 | | | 391 |
| Normal Compactness AVE 01pas | 16 | 16 | | 16 |
| Normal Compactness AVE 02pas | | 19 | | 17 |
| Normal Compactness AVE 03pas | | 19 | | 16 |
| Normal Compactness AVE 04pas | | 20 | | |
| Normal Compactness AVE 05pas | | 19 | | |
| Normal Compactness AVE 06pas | | 19 | | |
| Normal Compactness AVE 07pas | 16 | 17 | | |
| Normal Compactness AVE 08pas | 18 | 16 | | |
| Normal Compactness AVE 09pas | 20 | 17 | | |
| Normal Compactness AVE 10pas | 21 | 18 | | |
| Normal Compactness SD 01pas | | | 10 | 10 |
| Normal Compactness SD 02pas | | 9 | | 11 |
| Normal Compactness SD 03pas | | 9 | | 9 |
| Normal Compactness SD 04pas | | 10 | | 8 |
| Normal Compactness SD 05pas | | 10 | | 7 |
| Normal Compactness SD 06pas | | 10 | | |
| Normal Compactness SD 07pas | | 10 | | |
| Normal Compactness SD 08pas | 9 | 10 | | |
| Normal Compactness SD 09pas | | 11 | 12 | |
| Normal Compactness SD 10pas | | 11 | 12 | |

FIG. 8

| Cell | CA | CB | CC | CD |
|---|---|---|---|---|
| Area_1pas_1bin | 32 | 100 | 0 | 0 |
| Area_1pas_2bin | 134 | 101 | 32 | 306 |
| Area_1pas_3bin | 141 | 123 | 47 | 170 |
| Area_1pas_4bin | 118 | 118 | 47 | 81 |
| Area_1pas_5bin | 54 | 93 | 89 | 51 |
| Area_1pas_6bin | 20 | 32 | 125 | 32 |
| Area_1pas_7bin | 7 | 14 | 140 | 17 |
| Area_1pas_8bin | 4 | 7 | 119 | 18 |
| Area_1pas_9bin | 1 | 8 | 79 | 6 |
| Area_1pas_10bin | 2 | 2 | 71 | 8 |
| Area_1pas_11bin | 0 | 2 | 67 | 7 |
| Area_1pas_12bin | 0 | 2 | 144 | 26 |
| Compactness_1pas_1bin | 3 | 1 | 0 | 4 |
| Compactness_1pas_2bin | 167 | 170 | 103 | 343 |
| Compactness_1pas_3bin | 130 | 177 | 158 | 134 |
| Compactness_1pas_4bin | 75 | 100 | 179 | 49 |
| Compactness_1pas_5bin | 46 | 60 | 134 | 37 |
| Compactness_1pas_6bin | 34 | 44 | 93 | 37 |
| Compactness_1pas_7bin | 22 | 21 | 74 | 24 |
| Compactness_1pas_8bin | 8 | 11 | 67 | 25 |
| Compactness_1pas_9bin | 9 | 9 | 43 | 20 |
| Compactness_1pas_10bin | 8 | 5 | 37 | 8 |
| Compactness_1pas_11bin | 6 | 7 | 24 | 8 |
| Compactness_1pas_12bin | 5 | 6 | 48 | 35 |

PREDICTIVE ACCURACY OF CHANGES IN CELL QUALITY

| label | QUALITY A | QUALITY B | QUALITY C | QUALITY D | QUALITY E |
|---|---|---|---|---|---|
| AVERAGE OF CELL MORPHOLOGY | 87.5 | 79.2 | 75.0 | 75.0 | 100.0 |
| STANDARDIZED TYPE A | 79.2 | 75.0 | 81.3 | 93.8 | 100.0 |
| STANDARDIZED TYPE B | 87.5 | 75.0 | 93.8 | 93.8 | 100.0 |
| STANDARDIZED TYPE C | 87.5 | 75.0 | 87.5 | 87.5 | 100.0 |
| STANDARDIZED TYPE D | 83.3 | 45.8 | 87.5 | 87.5 | 100.0 |
| STANDARDIZED TYPE F | 91.7 | 66.7 | 93.8 | 93.8 | 100.0 |

UNIT : [%]

FIG. 18

RESULTS FROM PROFILING OF CELL QUALITY/CELL CULTURE REQUIREMENTS USING HIGH ORDER INFORMATION
(RESULTS FROM 55 TIMES OF DETERMINATION TRIALS DISPLAYS ARE SHOWN BY ■)

| True label / Predicted label | CELL A MEDIUM A | | | CELL B MEDIUM B | | | CELL C MEDIUM A | | | CELL C MEDIUM B | | | CELL C MEDIUM C | | | CELL D MEDIUM B | | |
|---|---|---|---|---|---|---|---|---|---|---|---|---|---|---|---|---|---|---|
| | 1 well | 2 well | 3 well | 1 well | 2 well | 3 well | 1 well | 2 well | 3 well | 1 well | 2 well | 3 well | 1 well | 2 well | 3 well | 1 well | 2 well | 3 well |
| CELL A MEDIUM A | ■ | ■ | ■ | | | | | | | | | | | | | | | |
| CELL B MEDIUM B | | | | ■ | ■ | ■ | | | | | | | | | | | | |
| CELL C MEDIUM A | | | | | | | ■ | ■ | ■ | | | | | | | | | |
| CELL C MEDIUM B | | | | | | | | | | ■ | ■ | ■ | | | | | | |
| CELL C MEDIUM C | | | | | | | | | | | | | ■ | ■ | ■ | | | |
| CELL D MEDIUM B | | | | | | | | | | | | | | | | ■ | ■ | ■ |

FIG. 29

\<EVALUATION RESULTS\>

PROBABILITY OF A CELL IN CULTURE BEING A MESENCHYMAL STEM CELL (FROM BONE MARROW) IS : 80%

| RANKING | HOMOLOGY SCORE | EVALUATION CRITERIA | Sample ID | CELL TYPE | ORIGIN | PASSAGE NUMBER | AGE | SEX | MEDIUM |
|---|---|---|---|---|---|---|---|---|---|
| 1 | 99 | | AD0023 | MESENCHYMAL STEM CELL | BONE MARROW | 3 | 42 | F | MSCGM |
| 2 | 80 | | AFP11002 | MESENCHYMAL STEM CELL | BONE MARROW | 3 | 34 | F | DMEM+10%FBS |
| 3 | 70 | | DJ3002 | MESENCHYMAL STEM CELL | ADIPOCYTE | 4 | 45 | F | F-media |
| 4 | 20 | | FD1003 | FIBROCYTE | DERMIS | 2 | 32 | M | DMEM+10%FBS |
| 5 | 20 | | JT10034 | MESENCHYMAL STEM CELL | ADIPOCYTE | 3 | 28 | M | MSCGM |
| 6 | 15 | | JS100002 | FIBROCYTE | DERMIS | 2 | 25 | F | DMEM+10%FBS |

THE QUALITY OF A CELL IN CULTURE IS : GRADE A
PROBABILITY OF BELONGING TO A MESENCHYMAL STEM CELL (FROM BONE MARROW) WITH HIGH GROWTH RATE/DEGREE OF DIFFERENTIATION IS 80%

ASSIGNMENT SPACE MAP :

ASSIGNMENT MAP :

IMAGE DB LINK :

Omics DB LINK :

Option DB LINK :

CLINICAL DB LINK :

Clinical results:

APPARATUS AND ANALYTICAL EVALUATION METHODS USING MORPHOLOGICAL FEATURE PARAMETERS OF A CELL OR CELL POPULATION

CROSS REFERENCE TO RELATED APPLICATIONS

The present application is the National Stage under 35 U.S.C. § 371 of PCT International Application No. PCT/JP2016/060146, filed Mar. 29, 2016, which claims the benefit of and priority to Japanese Application No. 2015-070319, filed Mar. 30, 2015, Japanese Application No. 2015-070320, filed Mar. 30, 2015 and Japanese Application No. 2015-070410, filed Mar. 30, 2015, which applications are incorporated herein by reference in their entirety.

TECHNICAL FIELD

The present invention relates to a cell-analyzing information generating apparatus, and a method and program of generating cell-analyzing information.

BACKGROUND ART

Traditionally, the cell-staining technology is widely used in the fields of detection of naturally occurring cancers in cancer research, discrimination of heterologous cells from therapeutic cells in regenerative medicine, and clinical studies of mesenchymal stem cells (MSC).

Cells are destroyed when stained by the aforementioned cell-staining technology. Further, staining reagents are expensive, and cell-staining procedures themselves are troublesome. Accordingly, the present inventors continuously strive to conduct studies to develop an inexpensive and simple technology for non-destructive analysis of cells (see Patent Documents 1 to 5).

Patent Document 1: Japanese Unexamined Patent Application, Publication No. 2011-232051
Patent Document 2: Japanese Unexamined Patent Application, Publication No. 2011-229413
Patent Document 3: Japanese Unexamined Patent Application, Publication No. 2011-229410
Patent Document 4: Japanese Unexamined Patent Application, Publication No. 2011-229409
Patent Document 5: Re-publication of PCT International Publication No. 2010/098105

DISCLOSURE OF THE INVENTION

Problems to be Solved by the Invention

However, depending on cell-analysis technologies, items to be analyzed widely vary, and a wide variety of analysis approaches and requirements are available even when the same item is analyzed. For this reason, a distinct analytical model needs to be pre-established for every analysis item, analysis approach, and different requirement. A different analytical model often requires a different cell-analyzing information compatible with that model. This means that the structure and type of cell-analyzing information are often different when an analytical model is different. As used herein, the term "cell-analyzing information" refers to information about a sample cell required for generating an analytical model, and/or information about a cell to be analyzed. For this reason, there have demands for efficiently generating compatible cell-analyzing information per different analytical model.

The present invention is made in view of the above circumstances. An object of the present invention is to efficiently generate compatible cell-analyzing information per different analytical model.

Means for Solving the Problems

In order to achieve the above object, a cell-analyzing information generating apparatus according to one aspect of the present invention includes: a feature-group information generating means configured to generate, as feature-group information, information including values of N types (wherein N represents an integer having a value of 1 or more) of feature parameters about a morphological feature of a single cell of a plurality of cells or a morphological feature of a cell population based on data of one or more cell images included in a unit, the one or more cell images in the unit being selected from cell images capturing the cell population including the cells as an imaging subject in accordance with a predetermined requirement; and an information acquiring means configured to acquire, as analyzing information for use in conducting predetermined cell analysis, information including values of M types (wherein M is an integer having a value independent of N) of parameters based on at least one of the N types of feature parameters included in the feature-group information.

A method and program of generating cell-analyzing information according to one aspect of the present invention are compatible with the aforementioned cell-analyzing information generating apparatus according to one aspect of the present invention.

Effects of the Invention

According to the present invention, compatible cell-analyzing information can be efficiently generated for per different analytical model.

BRIEF DESCRIPTION OF THE DRAWINGS

FIG. 4 schematically shows a mode of processing performed in the image quantification unit of the feature-group information generating unit in FIG. 3.

FIG. 5 illustrates 10 specific types of feature parameters.

FIG. 7 specifically shows some of the feature-group information.

FIG. 8 specifically shows some of the feature-group information.

FIG. 16 shows an example of a sample data set used for generation of an analytical model for predicting changes in cell quality.

FIG. 17 shows predictive accuracy when changes in cell quality are predicted using the sample data set in FIG. 16.

FIG. 18 shows results from actual prediction of changes in cell quality by the analytical model generated using the sample data set of the standardized type E in FIG. 17.

FIG. 29 shows an example of a screen in which output information is displayed.

PREFERRED MODE FOR CARRYING OUT THE INVENTION

Below, the embodiments of the present invention will be described with reference to the drawings.

Figure 1:
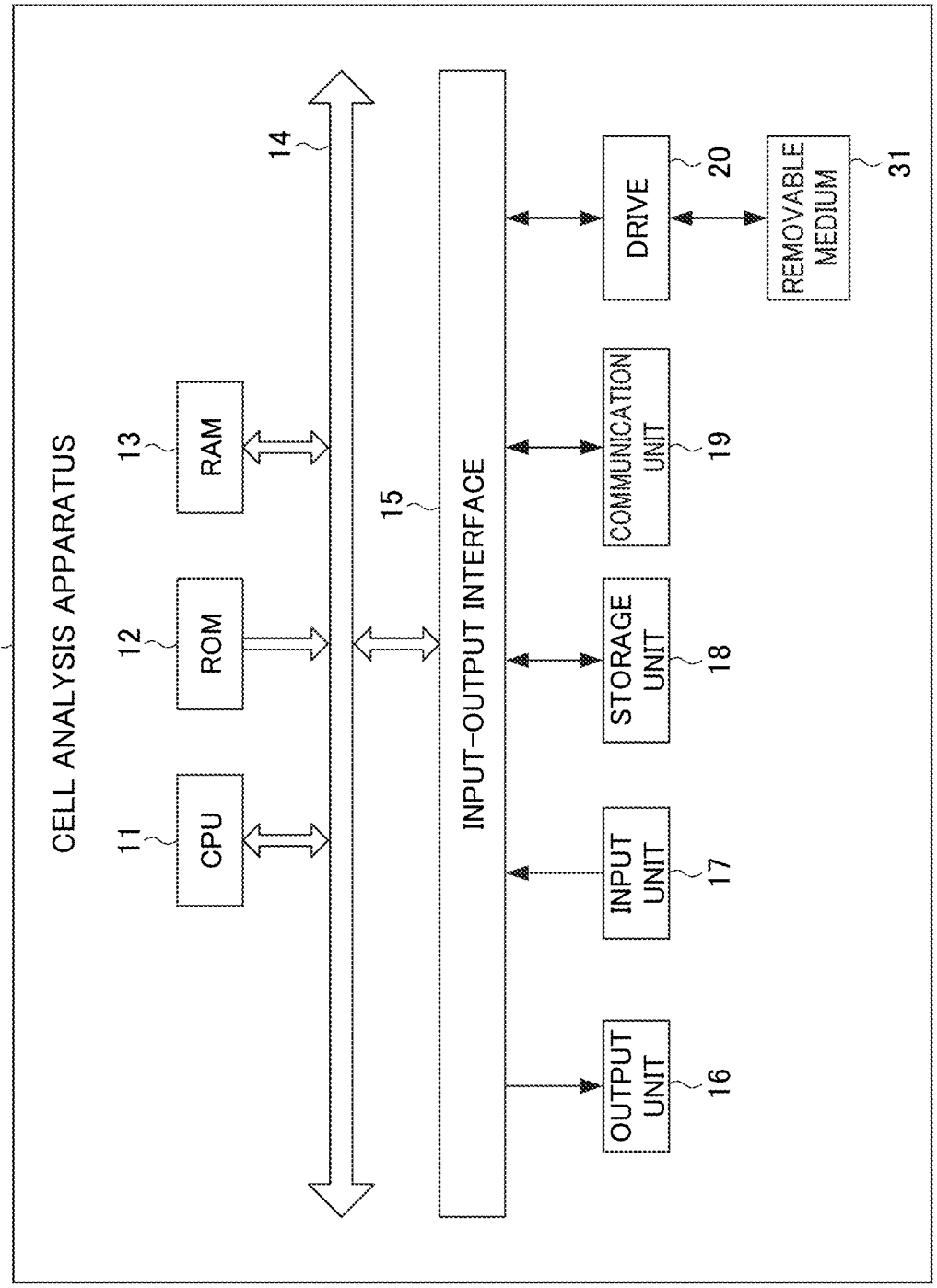
FIG. 1 is a block diagram showing the hardware configuration of a cell analysis apparatus according to one embodiment of the present invention.

FIG. 1 is a block diagram showing the hardware configuration of a cell analysis apparatus 1 according to one embodiment of the present invention. The cell analysis apparatus 1 includes a CPU (Central Processing Unit) 11, a ROM (Read Only Memory) 12, a RAM (Random Access Memory) 13, a bus 14, an input-output interface 15, an output unit 16, an input unit 17, a storage unit 18, a communication unit 19, and a drive 20.

The CPU 11 is configured to execute various types of processing according to a program stored in the ROM 12 or a program loaded to the RAM 13 from the storage unit 18. Data and others required for the CPU 11 to execute various types of processing are also stored in the RAM 13 in an appropriate manner.

The CPU 11, the ROM 12, and the RAM 13 are mutually connected through the bus 14. The input-output interface 15 is also connected to the bus 14. The output unit 16, the input unit 17, the storage unit 18, the communication unit 19, and the drive 20 are connected to the input-output interface 15.

The output unit 16 includes a display, a loudspeaker, and/or the like, and is configured to output various types of information in a form of images and/or sounds. The input unit 17 includes a keyboard, a mouse, and/or the like, and is configured to accept inputs of various types of information. The storage unit 18 includes a hard disk, a DRAM (Dynamic Random Access Memory), and/or the like, and is configured to store various types of data. The communication unit 19 is configured to control communication with other apparatuses (an external apparatus 81 and/or a pre-processing apparatus 82 as shown in FIG. 2 described below in the present embodiment) via a network (not shown).

A removable medium 31 may appropriately be mounted to the drive 20, if needed. A program read out from the removable medium 31 through the drive 20 may be installed in the storage unit 18, if needed. Further, various types of data stored in the storage unit 18 can also be stored in the removable medium 31 as in the storage unit 18.

Figure 2:
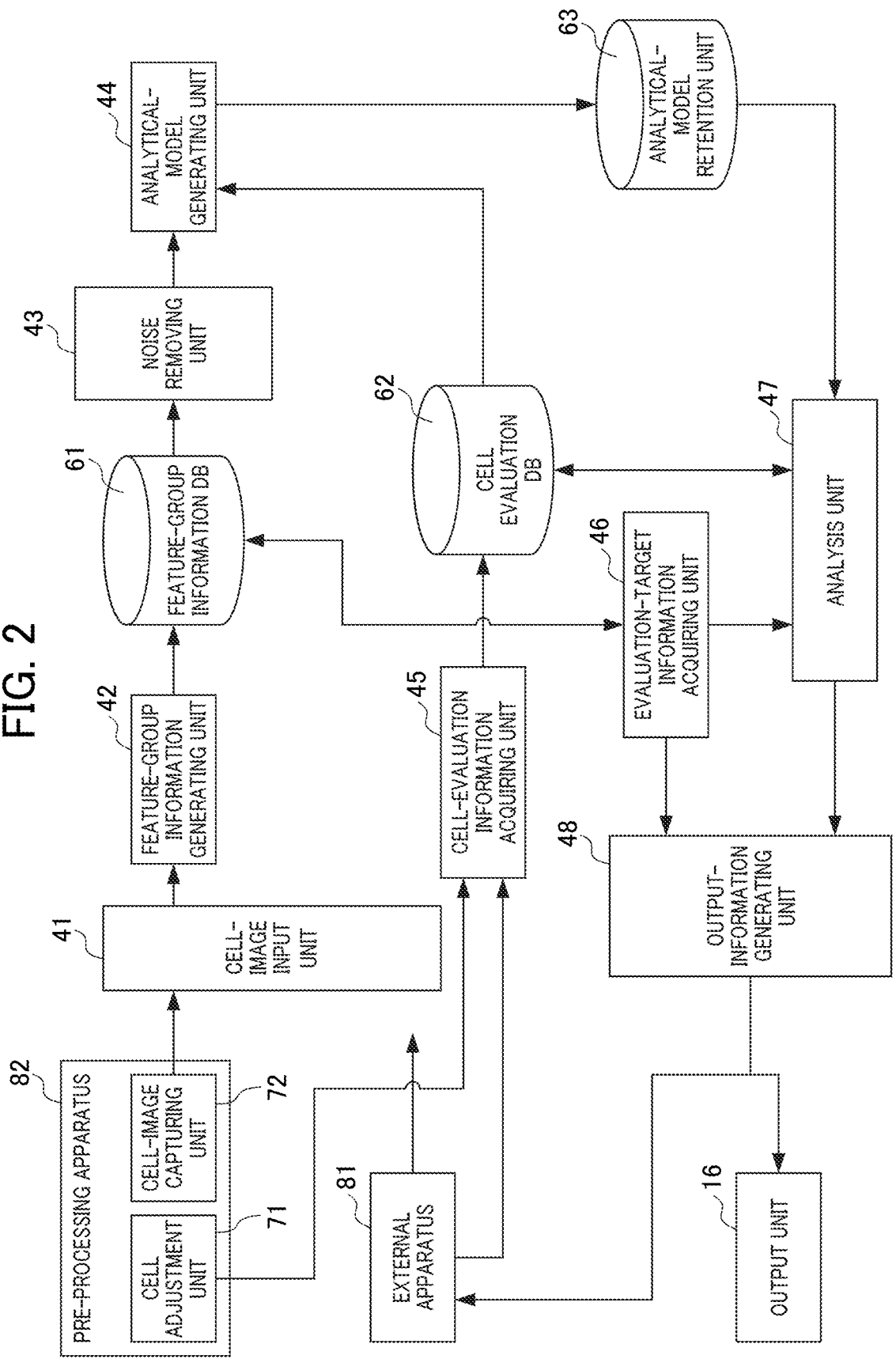
FIG. 2 is a functional block diagram showing a functional configuration for performing cell-analysis processing among the functional configurations of the cell analysis apparatus 1 in FIG. 1.

FIG. 2 is a functional block diagram showing a functional configuration for performing cell-analysis processing among the functional configurations of the cell analysis apparatus 1 of FIG. 1. The term "cell-analysis processing" refers to a series of processing ranging from performing predetermined analysis on one or more cells based on data of an image including the one or more cells as imaging subjects (hereinafter referred to as a "cell image") and a predetermined analytical model to outputting results therefrom. As used herein, the term "predetermined analysis on a cell" means any analysis based on a cell image including the cell as an imaging subject. That is, the term "predetermined analysis on a cell" encompasses a broad concept, including not only analyzing the type and/or requirements of the cell but also analyzing the outside (the surrounding environment and the like) of the cell.

When cell-analysis processing is performed, a cell-image input unit 41, a feature-group information generating unit 42, a noise removing unit 43, an analytical-model generating unit 44, a cell-evaluation information acquiring unit 45, an evaluation-target information acquiring unit 46, an analysis unit 47, and an output-information generating unit 48 mainly function in the CPU 11 as shown in FIG. 2. Further, feature-group information DB 61, cell evaluation DB 62, and an analytical-model retention unit 63 are provided in one region of the storage unit 18.

The cell-image input unit 41 is configured to input the data of a cell image. Here, there is no particular limitation for the source of a cell image, but it may be the external apparatus 81 connected via the Internet and the like (not shown), or it may be the pre-processing apparatus 82 under control of an administrator or others of the cell analysis apparatus 1. That is, a person who provides a cell image, who is hereinafter referred to as a "user", may operate the external apparatus 81 to provide the data of a cell image for the cell analysis apparatus 1 via the Internet and the like in a case where the user does not have the cell analysis apparatus 1. On the other hand, in a case where the user has the cell analysis apparatus 1, the user further has the pre-processing apparatus 82, and provide the cell analysis apparatus 1 with the data of a cell image created in the pre-processing apparatus 82. The pre-processing apparatus 82 has a cell adjustment unit 71 configured to adjust a cell, and a cell-image capturing unit 72 configured to capture an image of the above cell and output the data of the cell image.

The feature-group information generating unit 42 is configured to binarize the data of a cell image, and extract a cell object from the resulting data (hereinafter, referred to as the "binarized data"), and generate the data, i.e., quantified date, which includes values of parameters each representing each of one or more morphological features of that cell object.

It is noted that in particular, a parameter representing a predetermined morphological feature is hereinafter referred to as a "feature parameter." Further, the value of a feature parameter is also referred to as the "morphological feature quantity."

Here, a cell population including a plurality of cells, for example, a cell population cultured in the same container (the number of cells may change as a function of time) is often captured in one cell image as an imaging subject. In this case, a plurality of cell objects are included in a single cell image, and values of one or more feature parameters are each calculated for each of the cell objects.

When such a cell image is used in which a cell population is captured as an imaging subject, both of the value of a feature parameter (a morphological feature quantity) of a simple cell and the information about a feature parameter of the cell population (hereinafter referred to as the "population information") are significant information. Examples of the population information include, for example, a histogram of a predetermined feature parameter of a cell population and statistical values (values such as the average value and variance value) of a predetermined feature parameter of a cell population.

In the present embodiment, the value of a feature parameter of a single cell (a morphological feature quantity of a single cell) and population information are hereinafter collectively referred to "feature-group information."

Here, the feature-group information does not necessarily consist only of numerical values obtained from a single cell image. For example, when a cell population in a predetermined container is an imaging subject, cell images may be captured multiple times as a function of time. In such a case, feature-group information may be generated based on the data from a plurality of cell images captured at different time points. Further, feature-group information, for example, may be generated for the same type of cells separately cultured in different containers (wells and the like) based on the data of a plurality of cell images separately captured for each of the different containers. As described above, feature-group information may be generated based on data sets from any number of cell images.

The noise removing unit 43 is configured to remove data which may be considered as noise with respect to a sample data set for use in generating an analytical model. Data which may be considered as noise is, for example, the data of a cell image of poorly treated cell culture, i.e., a sample data set extracted from feature-group information and others generated based on the data of that cell image.

The analytical-model generating unit 44 is configured to generate a sample data set based on at least a portion of feature-group information stored in the feature-group information DB 61. Here, the phrase "generating a sample data set based on at least a portion of feature-group information" means not only simply extracting some of the constituent elements of feature-group information (the values of feature parameters) but also generating new data using any number and any type of constituent elements.

The analytical-model generating unit 44 is configured to generate a model (hereinafter referred to as an "analytical model") for performing predetermined analysis on a cell in a cell image using one or more sample data sets.

Again, there are a wide variety of analysis items depending on predetermined analysis on a cell. For example, three representative analysis items, among others, can be exemplified: identifying the type of a cell; determining requirements of a cell in culture; and analyzing the external environment of a cell in culture. Therefore, a plurality of analytical models may be present when there is a plurality of analysis items. That is, an analytical model for analyzing the type of a cell, an analytical model for determining requirements of a cell in culture, and an analytical model for analyzing the external environment of a cell in culture are often different in types. Further, a wide variety of analysis approaches, different requirements, and the like may be present even when the type of an analysis item is the same. Therefore, different types of analytical models are often used depending on analytical approaches and/or different requirements.

When the type of an analytical model is different, the type and structure of a sample data set used for generation thereof is also different in many cases. That is, the values of all types of feature parameters included in feature-group information are not always used directly as a sample data set. That is, for each of analysis items, analytical approaches, different requirements, and the like, combinations of different types and numbers of feature parameters may be extracted to generate a sample data set based on each extracted combination.

Specifically, suppose that there is feature-group information including, for example, the average value of sizes in a cell population (first feature parameter), the variance value of the sizes in the cell population (second feature parameter), the average value of lengths in the cell population (third feature parameter), and the variance value of the lengths in the cell population (fourth feature parameter). In this case, a sample data set for generating an analytical model for categorizing the type of a cell may be generated from each value of the first feature parameter and the third feature parameter. Alternatively, a sample data set for generating an analytical model for determining requirements of a cell in culture may be generated from each value of the second feature parameter, the third feature parameter, and the fourth feature parameter.

Here, the values of feature parameters in the feature-group information may be directly used as constituent elements of a sample data set. However, a value of a parameter other than the feature parameters in the feature-group information may be newly generated as a consistent element of a sample data set as described below with reference to FIGS. 25 to 27. That is, a sample data set including values of M types of parameters (M is an integer having a value of 1 or more independently of N) may be generated based on N types of feature parameters (N is an integer having a value of 1 or more) in feature-group information. The M types of parameters are a concept independent of the N types of feature parameters. That is, the types and number of M types of parameters constituting a sample data set are often different when analysis items, analysis approaches, different requirements, and the like are different.

Further, feature-group information as a basis of a sample data set may not necessarily be generated from a single cell image. That is, feature-group information is generated from a unit of one or more cell images selected based on a predetermined requirement. There is no particular limitation for the predetermined requirement as used herein, but "cell images at each of time points t1 to t5 in the same container" may be used a requirement. When the above requirement is used, one sample data set is generated based on the feature-group information obtained from 5 cell images of the same container captured at the time points t1 to t5.

Therefore, data (numerical values) at different time points may be included in a sample data set. Specifically, suppose that there is feature-group information including, for example, the first to fourth feature parameters as described in the above example. In addition, suppose that the third feature parameter is used as a parameter value for a sample data set both for an analytical model for categorizing the type of a cell and an analytical model for determining requirements of a cell in culture. Even in this case, the values at the time points of both t1 and t2 may be included when generating an analytical model for categorizing the type of a cell while the value at the time point t4 may be included when generating an analytical model for determining requirements of a cell in culture. That is, values from different time points are considered as independent sets of data each having a different meaning even for the same feature parameter. Therefore, a sample data set may be generated considering time dependent changes in each of analysis items, analysis approaches, different requirements, and the like.

Taken together, feature-group information is multidimensional information with N or more dimensions including at least N types of feature parameters as elements. A sample data set includes values of M types of parameters, and is generated based on at least one of the N types of feature parameters included in the aforementioned feature-group information. That is, the M types of parameters in the sample data set are independent of the N types of feature parameters, and may include several types of feature parameters among the N types of feature parameters as a matter of course, and may also include a parameter different from these. As used herein, a parameter other than the feature parameters is referred to as a "supplementary parameter." For example, a time-dependent parameter can be used as a supplementary parameter. For example, parameters defined by external environments, different requirements, and the like are also considered as supplementary parameters. In addition, for example, parameters representing axes which define a predetermined three-dimensional space are included as constituent elements in the sample data set sets of the examples in FIGS. 25 to 27 described below. These parameters representing the axes are also examples of the supplementary parameter.

As described above, a sample data set including, as elements, M types of parameters independent of feature-group information is used when generating an analytical model in the present embodiment instead of directly using feature-group information itself as a sample data set. With regard to the M types of parameters, combinations of any types and any number can be used depending on analysis items, analysis approaches, different requirements, and the like. That is, suitable sample data sets of different types and different structures per analysis item, analysis approach, predetermined requirement, and the like can be individually generated from an item of feature-group information. As a result, suitable analytical models can be generated per analysis item, analysis approach, predetermined requirement, and the like. That is, suitable sample data sets (one type of cell-analyzing information) per analytical model can be generated efficiently. This enables easy and appropriate cell analysis to be performed comprehensively in terms of each of analysis items, analysis approaches, predetermined requirements, and the like.

That is, in the analytical-model generating unit 44 shown in FIG. 2, the feature-group information DB 61 is searched for feature information about a sample cell population with regard to each of analysis items, analysis approaches, different requirements, and the like to generate a sample data set including, as elements, values of M types of parameters based on at least one of N types of feature parameters included in the feature-group information. Then, in the analytical-model generating unit 44, a plurality of analytical models corresponding to each of analysis items, analysis approaches, different requirements, and the like are generated using one or more sample data sets of different types and different structures depending on each of analysis items, analysis approaches, different requirements, and the like. Each of these analytical models is linked with the information about the type and structure of each sample data set, and retained in the analytical-model retention unit 63.

It is noted that once feature-group information about a new cell image is stored in the feature-group information DB 61, the analytical models retained in the analytical-model retention unit 63 are appropriately renewed by the analytical-model generating unit 44 at a subsequent proper timing.

The cell-evaluation information acquiring unit 45 is configured to acquire evaluation-target information corresponding to a cell image from the external apparatus 81 and/or the cell adjustment unit 71 of the pre-processing apparatus 82, and store it in the cell evaluation DB 62. The evaluation-target information corresponding to a cell image includes information about results from destructive cell evaluation performed on a cell population (for example, a cell population in a predetermined container) as an imaging subject for that cell image by a predetermined evaluation method. That is, the evaluation-target information represents information from analytical evaluation of a predetermined cell population performed by a different means than a cell image. There is no particular limitation for the destructive cell evaluation, and any can be used such as genome, gene expression, proteins, metabolic products, mutual arrogation effect, results from live organ transplant, and treatment outcomes. It is noted the evaluation-target information is suitably stored in the cell evaluation DB 62 as quantified information. This is because a value from the evaluation-target information can be included as an element value (a value of a predetermined parameter) of a sample data set (multidimensional information) when generating a predetermined analytical model.

The evaluation-target information acquiring unit 46 is configured to acquire feature-group information of a cell to be subjected to analytical evaluation from the feature-group information DB 61 in a form compatible with an analytical model for the analytical evaluation. It is noted that the information acquired in this way by the evaluation-target information acquiring unit 46 is hereinafter referred to as "evaluation-target information."

The term "form compatible with an analytical model for analytical evaluation" refers to a form similar to that of a sample data set used for generating that analytical model (i.e., a form in which the M types of parameters are of the same type). That is, as described above, a form of a sample data set used for generation may be different when the type of an analytical model is different. Therefore, the evaluation-target information also needs to be of a similar form as the sample data set used for generating an analytical model in use.

That is, the evaluation-target information acquiring unit 46 is configured to search the feature-group information DB 61 for feature-group information of a cell to be subjected to analytical evaluation to acquire information including M types of parameters as evaluation-target information based on at least one of the N types of feature parameters included in that feature-group information. In this case, "at least one of the N types of feature parameters included in that feature-group information" and the "M types of parameters" are of the same type as those used when generating the sample data set for the analytical model in use.

The analysis unit 47 is configured to perform analytical processing of a cell to be subjected to analytical evaluation based on the evaluation-target information and the analytical model. As described above, there is no particular limitation for the analysis items, analysis approaches, different requirements, and the like, and thus a wide variety of analyses can be performed.

The output-information generating unit 48 is configured to generate, as output information, information (for example, evaluation-target information) about a cell to be subjected to analytical evaluation, and information including results from the analytical processing of that cell. Then, the output-information generating unit 48 outputs the output information to the output unit 16 or the external apparatus 81. It is noted that specific examples of output information will be described below with reference to FIGS. 28 and 29.

Hereinabove, an exemplary functional configuration of the cell analysis apparatus 1 is described with reference to FIG. 2. Next, a detailed configuration of the feature-group information generating unit 42 in the cell analysis apparatus 1 having a functional configuration as shown in FIG. 2 will be described with reference to FIG. 3.

Figure 3:
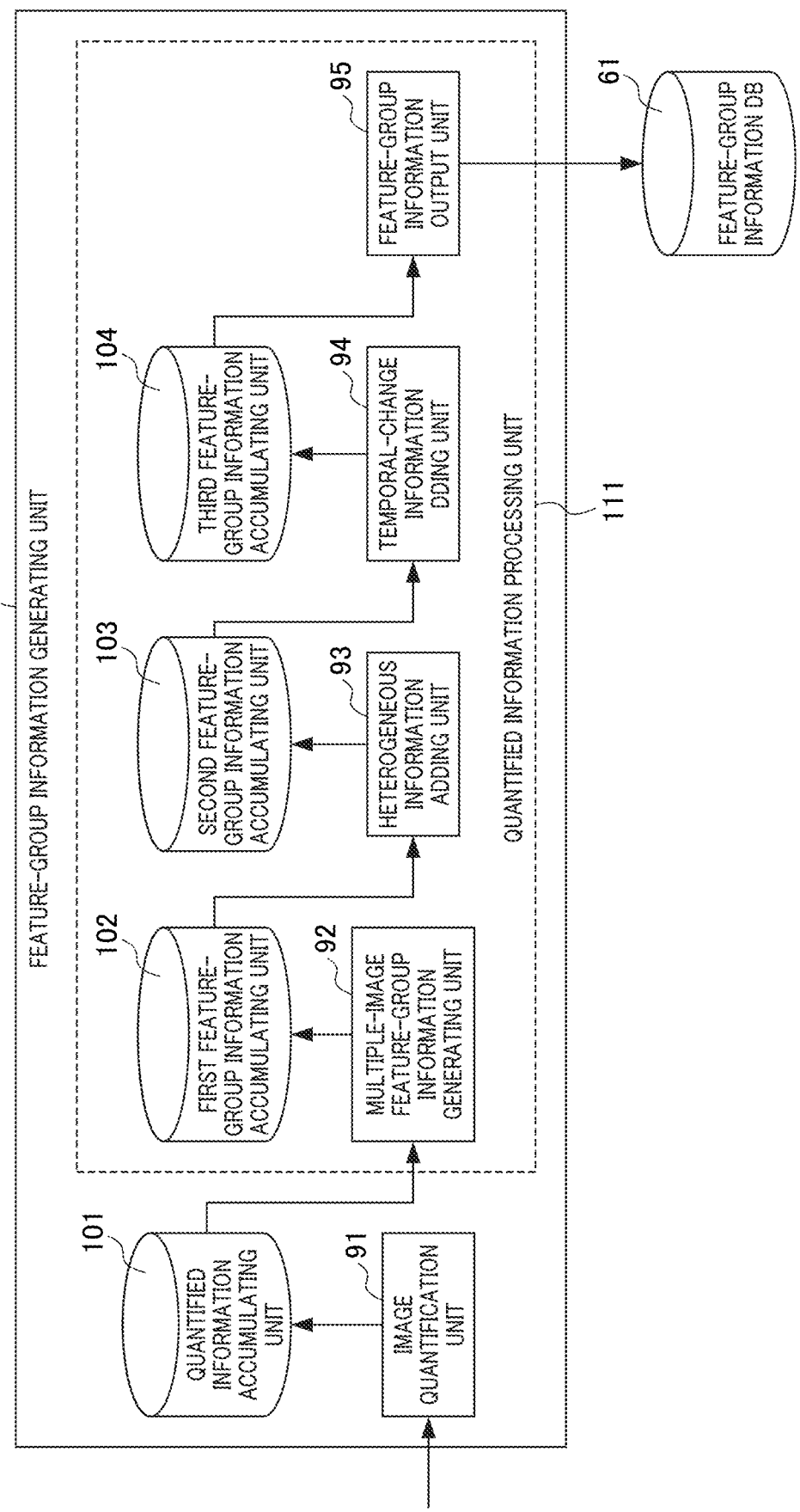
FIG. 3 is a functional block diagram showing in detail the functional configuration of the feature-group information generating unit among the functional configuration of the cell analysis apparatus 1 shown in FIG. 2.

FIG. 3 is a functional block diagram showing in detail the functional configuration of the feature-group information generating unit 42 in the functional configuration of the cell analysis apparatus 1 as shown in FIG. 2.

As shown in FIG. 3, an image quantification unit 91, a multiple-image feature-group information generating unit 92, a heterogeneous information adding unit 93, a temporal-change information adding unit 94, and a feature-group information output unit 95 in the feature-group information generating unit 42 function in the CPU 11 (FIG. 1). Further, a quantified information accumulating unit 101, a first feature-group information accumulating unit 102, a second feature-group information accumulating unit 103, and a third feature-group information accumulating unit 104 are provided in one region of the storage unit 18 (FIG. 1).

The image quantification unit 91 is configured to perform predetermined image processing on a unit of processing, the unit of processing being data of a single cell image, to generate feature-group information for that unit of processing. The feature-group information generated from a single cell image, i.e., the information including a collection of values (numerical values) of various feature parameters of each of cell objects included in that cell image, is accumulated in the quantified information accumulating unit 101. That is, the quantified information accumulating unit 101 is configured to accumulate a plurality of units of feature-group information, each of the units being derived from a single cell image.

FIG. 4 schematically illustrates a mode of processing performed in the image quantification unit 91. In the example of FIG. 4, the data of a single cell image G1 is given to the image quantification unit 91 as a unit of processing. The image quantification unit 91 is configured to generate a binarized data G2 from the data of the cell image G1. The image quantification unit 91 is configured to extract the "XXX" number of candidate cell objects (XXX is any integer value) from the binarized data. Here, the term "candidate cell objects" is used instead of "cell objects" because objects which are not cells, but is noise (hereinafter referred to "noise objects") are included.

The image quantification unit 91 is configured to assign a unique ID (Cell ID) to each of the candidate cell objects, and obtain various feature parameters for each. That is, each of the cell objects will be quantified. In the example of FIG. 4, values of 9 types of feature parameters (Parameters 1 to 9) are determined for each of the cell objects. This comprehensive list covering values (quantified data) of 9 types of feature parameters for each of the cell objects corresponds to feature-group information I1 of the cell image G1.

However, the quantified data (values of 9 types of feature parameters) from a noise object is also included in the feature-group information I1 of the cell image G1. Therefore, the image quantification unit 91 is configured to distinguish a noise object from candidate cell objects in accordance with an appropriate algorithm in a step S1 to remove that noise object from the quantified data. In the example of FIG. 4, the candidate cell objects having IDs of "Cell 001" and "Cell 002" are determined as noise objects. For this reason, the quantified data of these noise objects is removed from the feature-group information I1 of the cell image G1 to generate feature-group information I2 of the cell image G1.

Further, the image quantification unit 91 is configured to distinguish a noise object from candidate cell objects in a step S2 in accordance with an appropriate algorithm different from that used in the step S1 to remove that noise object from the quantified data. In the example of FIG. 4, the candidate cell objects having IDs of "Cell 003" and "Cell 004" are determined as noise objects. For this reason, the quantified data of these noise objects is removed from the feature-group information I1 of the cell image G1 to generate feature-group information I3 of the cell image G1.

The image quantification unit 91 is configured to definitively accept the candidate cell objects from which the noise objects have been removed as cell objects in a step S3, and store the feature-group information I3 of the cell image G1 in the quantified information accumulating unit 101.

It is noted that the number of the types of feature parameters is 9 in the example shown in FIG. 4, but the number is not limited to this. For example, FIG. 5 shows 10 specific types of feature parameters. In FIG. 5, one predetermined type of a feature parameter is listed in each row. The item in the first column represents a parameter number. The item in the second column represents the name of a feature parameter. The item in the third column represents an example of a feature parameter (or a method of computation). The item in the fourth column represents the description of a feature parameter.

The term "Total area" refers to a feature parameter which represents the area of a cell (more precisely a "cell object," but simply refers to a "cell" in this paragraph). The term "Area" is a feature parameter which represents the area except for a "Hole" in a cell. Here, the term "Hole" is a portion in which the brightness of a cell image is at or above the threshold value in terms of contrast (a portion which appears near white under phase-contrast observation). The term "Perimeter" is a feature parameter which represents the length of the outer periphery of a cell. The term "Length" is a feature parameter which represents the maximum value of a line crossing a cell (the entire length of a cell). The term "Breadth" is a feature parameter which represents the maximum value of a line orthogonal to "Length" (the breadth of a cell). The term "Inner radius" is a feature parameter which represents the radius of the inner periphery of a cell. The term "Elliptical form factor" is a feature parameter obtained by dividing a value of "Length" by that of "Breadth." The term "Fiber Breadth" is a feature parameter which represents the width of a cell when the cell is assumed to be pseudo-linear (the length in the direction perpendicular to Fiber Length). The term "Fiber Length" is a feature parameter which represents the length of a cell when the cell is assumed to be pseudo-linear. The term "Shape Factor" is a feature parameter which represents the circularity of a cell (the roundness of a cell).

It is noted that the feature parameters exemplified in FIG. 5 are merely illustrative, and any types of feature parameters can be used as long as they represent predetermined morphological features which can be quantified from a cell object. Further, a cell population is included in a single cell image, and thus population information may also be obtained to be included in the feature-group information although not shown here. For example, the average value, variance value, and the like of the aforementioned "Total area" may be included in the feature-group information. Moreover, a histogram of a predetermined morphological feature quantity for a plurality of cells may be obtained, and the values in each bin of the histogram and others may be included in the feature-group information.

Returning to FIG. 3, the multiple-image feature-group information generating unit 92 is configured to determine a first unit of processing including a plurality of cell images in accordance with a predetermined rule, and obtain the feature-group information included in the first unit of processing from the quantified information accumulating unit 101. There is no particular limitation for the predetermined rule, but a rule is used here in which a plurality of cell images captured at the same time point under the same requirements are considered as the first unit of processing. Next, in the multiple-image feature-group information generating unit 92, multiple sets of quantified data included in each feature-group information obtained from the quantified information accumulating unit 101 are combined and/or rearranged to generate feature-group information in the first unit of processing. The feature-group information in the first unit of processing is accumulated in the first feature-group information accumulating unit 102.

The heterogeneous information adding unit 93 is configured to determine a second unit of processing including a plurality of cell images in accordance with a predetermined rule, and obtain each feature-group information included in the second unit of processing from the first feature-group information accumulating unit 102. There is no particular limitation for the predetermined rule, but a rule is used here in which a plurality of cell images captured at the same time point under multiple requirements are considered as the second unit of processing. Next, in the heterogeneous information adding unit 93, multiple sets of quantified data included in each feature-group information obtained are combined and/or rearranged to generate feature-group information as the second unit of processing to which heterogeneous information has been added. It is noted that specific examples of the heterogeneous information and the feature-group information as the second unit of processing will be described below with reference to FIG. 12. The feature-group information as the second unit of processing is accumulated in the second feature-group information accumulating unit 103.

The temporal-change information adding unit 94 is configured to determine a third unit of processing including a plurality of cell images in accordance with a predetermined rule, and obtain each feature-group information included in the third unit of processing from the second feature-group information accumulating unit 103. There is no particular limitation for the predetermined rule, but a rule is used here in which a plurality of cell images captured at multiple time points (different time points which change over time) under multiple requirements are considered as the third unit of processing. Next, in the temporal-change information adding unit 94, multiple sets of quantified data included in each feature-group information obtained are combined and/or rearranged to generate feature-group information as the third unit of processing to which the concept of a temporal change has been introduced. It is noted that specific examples of the feature-group information as the third unit of processing to which the concept of a temporal change has been introduced will be described below with reference to FIGS. 9 to 12. The feature-group information as the third unit of processing is accumulated in the third feature-group information accumulating unit 104.

The feature-group information output unit 95 is configured to obtain feature-group information from the third feature-group information accumulating unit 104 in an appropriate timing, and perform noise removal, addition of tag information, and/or the like, and then store it in the feature-group information DB 61.

As described when the feature-group information generating unit 42 is described in detail with reference to FIG. 3, the data of a single cell image is subjected to image processing in the image quantification unit 91, and converted into quantified feature-group information. Therefore, a target of the processing from the multiple-image feature-group information generating unit 92 to the feature-group information output unit 95 is not the data of an image (an image data) but feature-group information as quantified data. Therefore, the multiple-image feature-group information generating unit 92 to the feature-group information output unit 95 are collectively called a "quantified information processing unit 111" if appropriate.

Figure 6:
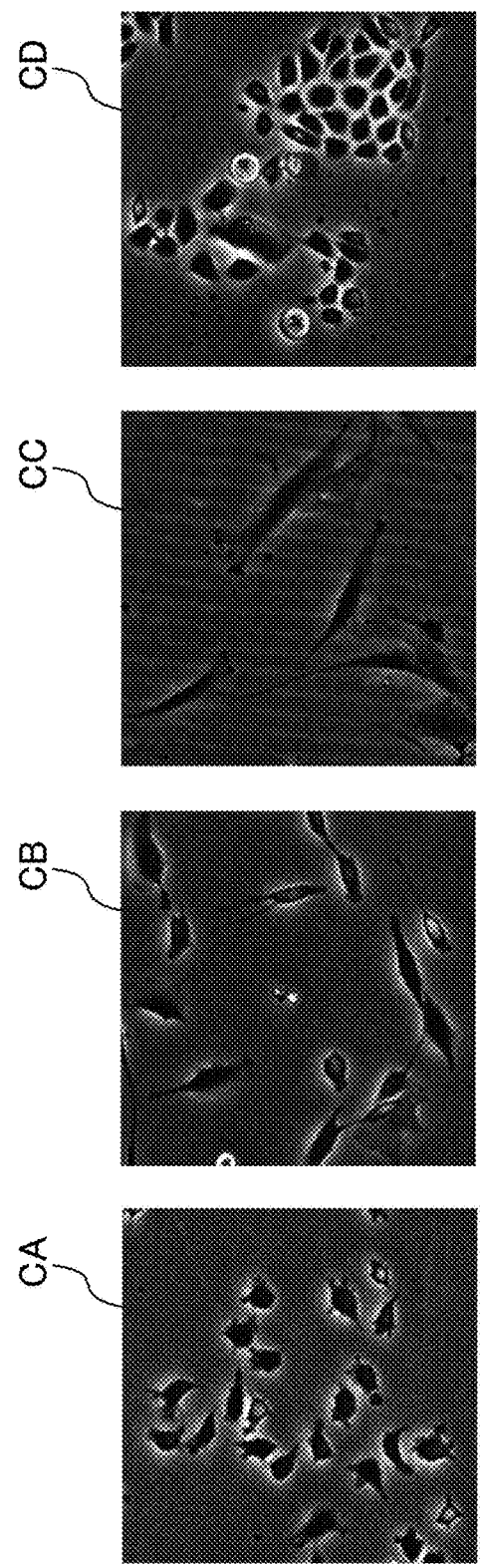
FIG. 6 shows an example of a cell image as a basis of generating feature-group information.

Here, with reference to FIGS. 6 to 8, specific examples of the feature-group information to be stored in the feature-group information DB 61 are described. FIG. 6 represents examples of cell images used as the basis of generating feature-group information. A cell image CA represents an image capturing the "CA" type of a cell population cultured in the same container. A cell image CB represents an image capturing the "CB" type of a cell population cultured in the same container. A cell image CC represents an image capturing the "CC" type of a cell population cultured in the same container. A cell image CD represents an image capturing the "CD" type of a cell population cultured in the same container. It is noted that in the example of FIG. 6, only one cell image is shown for each of the types "CA" to "CD," but actually 10 cell images are presumably present which are captured at each timing of separate time points t1 to t10 for each type. It is noted that the term "time point" used herein is not absolute time (the global standard time), but a time point relative to the predetermined standard time (time at which culture started), for example, 1 hour after the start of culture, and so on.

FIGS. 7 and 8 show some specific contents of feature-group information. There is no particular limitation for the unit of feature-group information as described above, but in the examples of FIGS. 7 and 8, the type of a cell is considered as one unit, and 4 units of feature-group information are each shown per column. That is, some contents of the feature-group information of the "CA" type of a cell are shown in the first column from the left (the item name is not counted). Some contents of the feature-group information of the "CB" type of a cell are listed in the second column from the left. Some contents of the feature-group information of the "CC" type of a cell are listed in the third column from the left. Some contents of the feature-group information of the "CD" type of a cell are listed in the fourth column from the left.

In the example of FIG. 7, shown are some contents including, as elements, statistical values of predetermined feature parameters for a cell population in each cell image among the feature-group information. The names of elements in the feature-group information are included in the leftmost column of FIG. 7. As used herein, the term "pas" refers to a time point (relative). That is, k pas (k is any integer having a value of 1 to 10) means that a value is obtained from a cell image captured at a time point of k. The terms "AVE" and "SD" represent the average value and the standard deviation, respectively. For example, the element (Normal_Area_AVE_01pas) in the first row from the top represents the average value of "Area" of a normal cell population included in a cell image at a time point of t1. Further, for example, the element (Normal_Area_SD_02pas) in the 12th row from the top represents the standard deviation of "Area" of a normal cell population included in a cell image at a time point t2.

In the example of FIG. 8, shown are some contents including, as elements, bins of histograms for predetermined feature parameters for a cell population in each cell image among the feature-group information. The names of elements in the feature-group information are included in the leftmost column of FIG. 8. As used herein, the term "bin" refers to the numerical code of a bin. There is no particular limitation for the way of numbering, but bins in a histogram having 12 sections (12 bins) are sequentially numbered from the left in the example of FIG. 8. For example, the element (Area_1pas_1bin) in the first row from the top represents a value of the first bin from the left among the histogram for the "Area" of a cell population included in a cell image captured at a time point t1.

Here, in FIGS. 7 and 8, each of the elements (each of the feature parameters) of feature-group information is differently colored and shaded according to their numerical values. Patterns of colors and shadings in a certain region may be distinct or characteristic for each of the "CA" to "CD" types of cells. As used herein, the term "certain region" may be a continuous region including a plurality of items which is continuous in the column direction, or may be a region composed of a plurality of discontinuous items. For example, the continuous region from the first row to the tenth row from the top in FIG. 7 (a portion of Normal_Area_AVE) may be considered as a "certain region." Further, for example, discontinuous portions at the time points t1 and t3 (discontinuous regions under the item names of 01pass1 and 03pass3) may constitute a "certain region." Here, for example, patterns of colors and shadings which enable easy categorization of the "CA" to "CD" types of cells are presumably present in a "certain portion" of feature-group information. In this case, categorization of the "CA" to "CD" types of cells can be easily performed by visually comparing the patterns (in actual processing, by calculating similarity) of colors and shadings in the "certain regions." That is, when generating and/or renewing an analytical model for categorizing the "CA" to "CD" types of cells, a sample data set is generated based on a value of each item (a value of each feature parameter) in the "certain region." Further, when a cell image including unknown cells as imaging subjects is an evaluation target, and these unknown cells are categorized into any of the "CA" to "CD" types, evaluation-target information is obtained based on a value of each item (a value of each feature parameter) in a "certain region" among the feature-group information of the evaluation target. That is, evaluation-target information having the same form as a sample data set is obtained.

Again, a "certain region" in feature-group information varies depending on the type of an analytical model, i.e., depending on analysis items, analysis approaches, different requirements, and the like.

Here, the amount of data in feature-group information is discussed. When there is no particular limitation for the number of dimensions N (the capacity of data) in feature-group information, collective information (hereinafter referred to as the "entire information") including each and every value of every feature parameter obtained from a cell image can be used. However, the number of dimensions N in feature-group information (the capacity of data) may actually be limited in some cases. In these cases, a portion of the collective information including each and every value of every feature parameter obtained from a cell image needs to be selected to use as feature-group information. On the other hand, when the amount of information in feature-group information is too limited, high-accuracy analysis cannot be achieved. That is, feature-group information needs to be generated so as to include population information suitable for analysis items, analysis approaches, different requirements, and the like selected from all possible combinations of types of population information.

Figure 9:
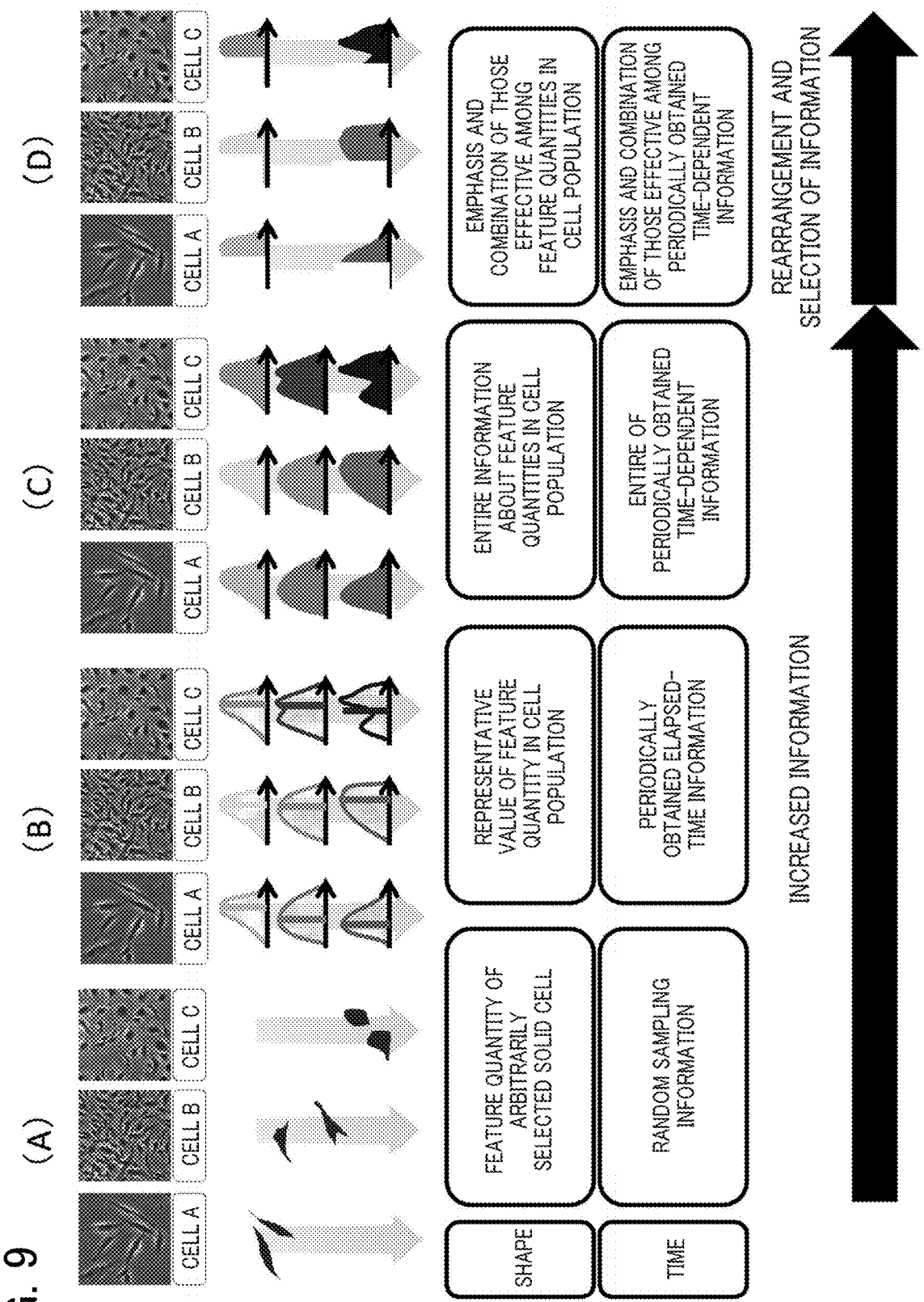
FIG. 9 is a schematic diagram illustrating differences in the elements extracted as feature-group information for analytical evaluation.

FIG. 9 is a schematic diagram illustrating differences in the elements extracted as feature-group information for analytical evaluation. For example, categorization of the cell types "A", "B", and "C" is assumed in the example of FIG. 9.

In the example of (A) of FIG. 9, the values of a feature parameter for two isolated cells selected arbitrarily in terms of a shape, and extracted randomly in terms of time direction from the entire information are used as feature-group information. Specifically, the feature-group information of the "A" type of cells, for example, is generated from data in which values of a feature parameter for two isolated cells are extracted, the two isolated cells (objects) being arbitrarily selected from a large number of cells (objects) within a cell image captured at an early timing in terms of time. In this case, a large number of cell objects are included in a single cell image, and values of a feature parameter are varied even though they are of the same type "A." Therefore, the values of a feature parameter for two isolated cells arbitrarily extracted may not necessarily be representative values for the type "A." Further, values of a feature parameter may change over time. Therefore, the values of a feature parameter for two isolated cells extracted at a random temporal timing may not necessarily be representative values for the type "A." For these reasons, accurate categorization of the cell types "A", "B", and "C" is often difficult when only the values of a feature parameter for several isolated cells arbitrarily selected without taking temporal changes into consideration are used as feature-group information.

Therefore, values of each feature parameter are extracted in view of a cell population included in a single cell image and in view of temporal changes, and a collection of these values can be used as feature-group information. For example, in the example of (B) of FIG. 9, elapsed-time information (a collection in the time direction) in which representative values of feature quantities of a cell population are extracted from the entire information in terms of a shape and the representative values of the feature quantities are periodically extracted in terms of time is used as feature-group information. For example, in the example of (C) of FIG. 9, elapsed-time information (a collection in the time direction) in which the whole information about feature quantities of a cell population is extracted from the entire information in terms of a shape, and the whole information about the feature quantities is periodically extracted in terms of time is used as feature-group information. Here, as shown in FIG. 9, the amount of information (the number of dimensions N) in feature-group information increases in the following order: (A)<(B)<(C) in FIG. 9.

However, as described above, the number of dimensions N of feature-group information (the capacity of data) is limited in many cases. In order to deal with such limitation, information in the entire information needs to be rearranged and selected, and more suitable parameter values need to be extracted to generate feature-group information as shown in the example of (C) of FIG. 9. That is, for example, as shown in the example of (D) of FIG. 9, elapsed-time information (a collection in the time direction) in which data obtained by a process of emphasizing and combining effective feature quantities among the feature quantities of a cell population are extracted from the entire information in term of a shape, and data obtained by a process of emphasizing and combining effective feature quantities among the feature quantities of the cell population are periodically extracted in terms of time is used as feature-group information.

Further, an approach for generating feature-group information based on emphasis and combination of effective feature quantities among the feature quantities of a cell population will be described with reference to FIGS. 10 to 12.

Figure 10:
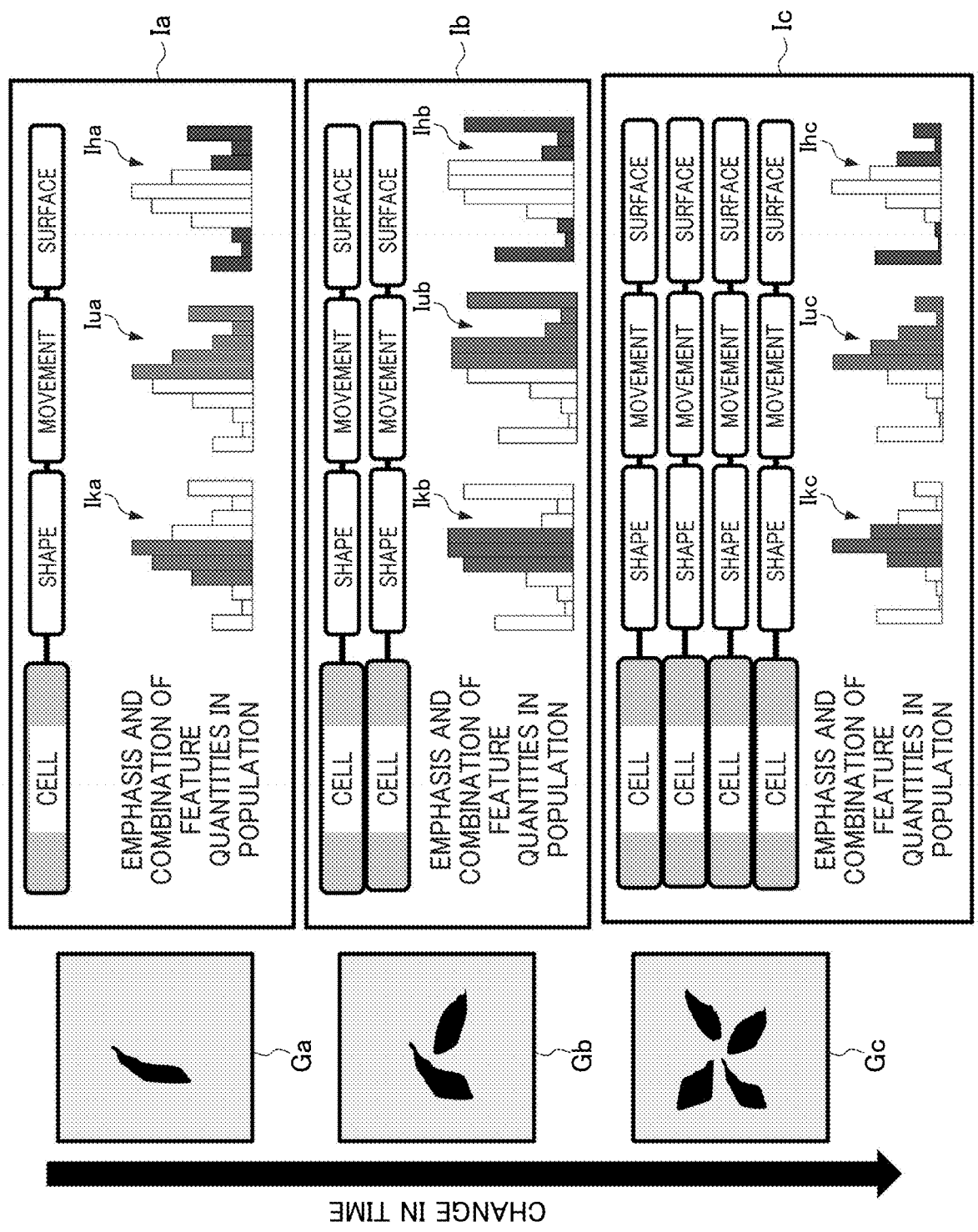
FIG. 10 schematically shows feature-group information generated from a cell image based on emphasis and combination of effective feature quantities among the feature quantities of a cell population.

FIG. 10 schematically shows feature-group information generated from a cell image based on emphasis and combination of effective feature quantities among the feature quantities of a cell population. In the example of FIG. 10, a cell population of the same type is assumed to be cultured in a predetermined container, and the number of cells is assumed to increase over time. That is, in FIG. 10, it appears that only one cell is shown in a cell image Ga, and only two cells are shown in a cell image Gb, and only four cells are shown in a cell image Gc. However, as a matter of course, the cell population is actually contained in the predetermined container as shown in the cell image G of FIG. 11. That is, the cells in FIG. 10 are not intended to represent individual cells, but to represent the rate (=1:2:4) of increase per hour.

Feature-group information Ia is obtained from the cell image Ga captured at a first time point. The feature-group information Ia includes at least three morphological feature quantities: the shape, movement, and surface of each cell and the population information of the cell population as the N types of feature parameters (elements). Here, examples of "population information" include statistical values such as the average value and the variance value, bin values of a histogram, and the like. For example, numerical data Ika obtained from a histogram for the "shape" of a cell population, numerical data Iua obtained from a histogram for the "movement" of the cell population, and numerical data Iha obtained from a histogram for the "surface" of the cell population are included in the feature-group information Ia as population information.

Here, shaded bins among those constituting each histogram correspond to information to be included in the feature-group information Ia (one bin corresponds to one type of a predetermined feature parameter when the bin is assumed to be one element). Here, in the histogram for the "shape" of the cell population, three bins left to the center are considered to be a "shape" feature. In other words, the "shape" feature may be diluted when the whole histogram is considered. Therefore, the three bins left to the center are extracted in order to "emphasize" the shape" feature. In contrast, unlike the case of the "shape", 5 bins in the right side are extracted as bins used to "emphasize" the "movement" feature. Moreover, unlike the cases of the "shape" and "movement", 6 bins at the both ends are extracted as bins used to "emphasize" the "surface" feature. Items of information (extracted bins) each emphasizing one of these features (shape, movement, and surface) correspond to the numerical data Ika, the numerical data Iua, and the numerical data Iha, respectively. Then, the feature-group information Ia is constructed by "combining" the numerical data Ika, the numerical data Iua, and the numerical data Iha.

Feature-group information Ib is obtained from the cell image Gb captured at a second time point. The feature-group information Ib includes at least three morphological feature quantities: the shape, movement, and surface of each cell and the population information of a cell population as the N types of feature parameters (elements). For example, numerical data Ikb obtained from a histogram for the "shape" of a cell population, numerical data Iub obtained from a histogram for the "movement" of the cell population, and numerical data Ihb obtained from a histogram for the "surface" of the cell population are included in the feature-group information Ib as population information. That is, items of information (extracted bins) each emphasizing one of these features (shape, movement, and surface) correspond to the numerical data Ikb, the numerical data Iub, and the numerical data Ihb, respectively. Then, the feature-group information Ib is constructed by "combining" the numerical data Ikb, the numerical data Iub, and the numerical data Ihb.

Feature-group information Ic is obtained from the cell image Gc captured at a third time point. The feature-group information Ic includes at least three morphological feature quantities: the shape, movement, and surface of each cell and the population information of a cell population as the N types of feature parameters (elements). For example, numerical data Ikc obtained from a histogram for the "shape" of a cell population, numerical data Iuc obtained from a histogram for the "movement" of the cell population, and numerical data Ihc obtained from a histogram for the "surface" of the cell population are included in the feature-group information Ic as population information. That is, items of information (extracted bins) each emphasizing one of these features (shape, movement, and surface) correspond to the numerical data Ikc, the numerical data Iuc, and the numerical data Ihc, respectively. Then, the feature-group information Ic is constructed by "combining" the numerical data Ikc, the numerical data Iuc, and the numerical data Ihc.

As described above, a pattern of emphasizing information in a distribution, i.e., a pattern of which bin is emphasized in a histogram varies depending on the features (shape, movement, and surface). Such a pattern is not limited to the aforementioned three types in the example of FIG. 10, but any types can be selected. FIG. 11 shows various specific examples of patterns for emphasizing information in a distribution. In FIG. 11, (A) shows a pattern in which the entire distribution information about a histogram is used. Here, as a histogram, both of absolute-value information (a histogram in which the numbers obtained from the cell image G of FIG. 11 are used directly) and information standardized and normalized against the reference value within a data base (a histogram in which the numbers obtained from the cell image G of FIG. 11 are normalized) are selectively used. In FIG. 11, (B) shows a pattern in which the average/median value of a histogram is used. In FIG. 11, (C) shows a pattern in which information within the 80% confidence interval in a histogram (a distribution) is used. In FIG. 11, (D) shows a pattern in which information above the average value in a histogram (a distribution) is used. In FIG. 11, (E) shows a pattern in which information outside the 80% confidence interval in a distribution is used.

When generating feature-group information (or when extracting a sample data set as described below), the optimal combination of an index (pattern) and an elapsed-time point for each of the features (shape, movement, and surface) or analysis items, analysis approaches, and various requirement are selected from the entire of these patterns. It is noted that the elapsed-time point will be described below with reference to FIG. 12.

Here, each of the feature-group information Ia to Ic in FIG. 10 corresponds to the quantified information formed from a single cell image in the image quantification unit 91 in the example of FIG. 3, and is to be accumulated in the quantified information accumulating unit 101. Therefore, as described above with reference to FIG. 3, when other cell images captured at the same time under the same requirement (for example, cell images of a plurality of wells) are present, each of the feature-group information Ia to Ic may be rearranged or combined with the feature-group information of the above other cell images in the multiple-image feature-group information generating unit 92, and the resulting first unit of feature-group information is accumulated in the first feature-group information accumulating unit 102. The heterogeneous information adding unit 93 will be described below with reference to FIG. 12. Now, processing performed at the temporal-change information adding unit 94 is described. The temporal-change information adding unit 94 is configured to process population information among each of the feature-group information Ia to Ic (combined, rearranged, and/or the like) in view of temporal changes to generate a third unit of processing of feature-group information.

Figure 12:
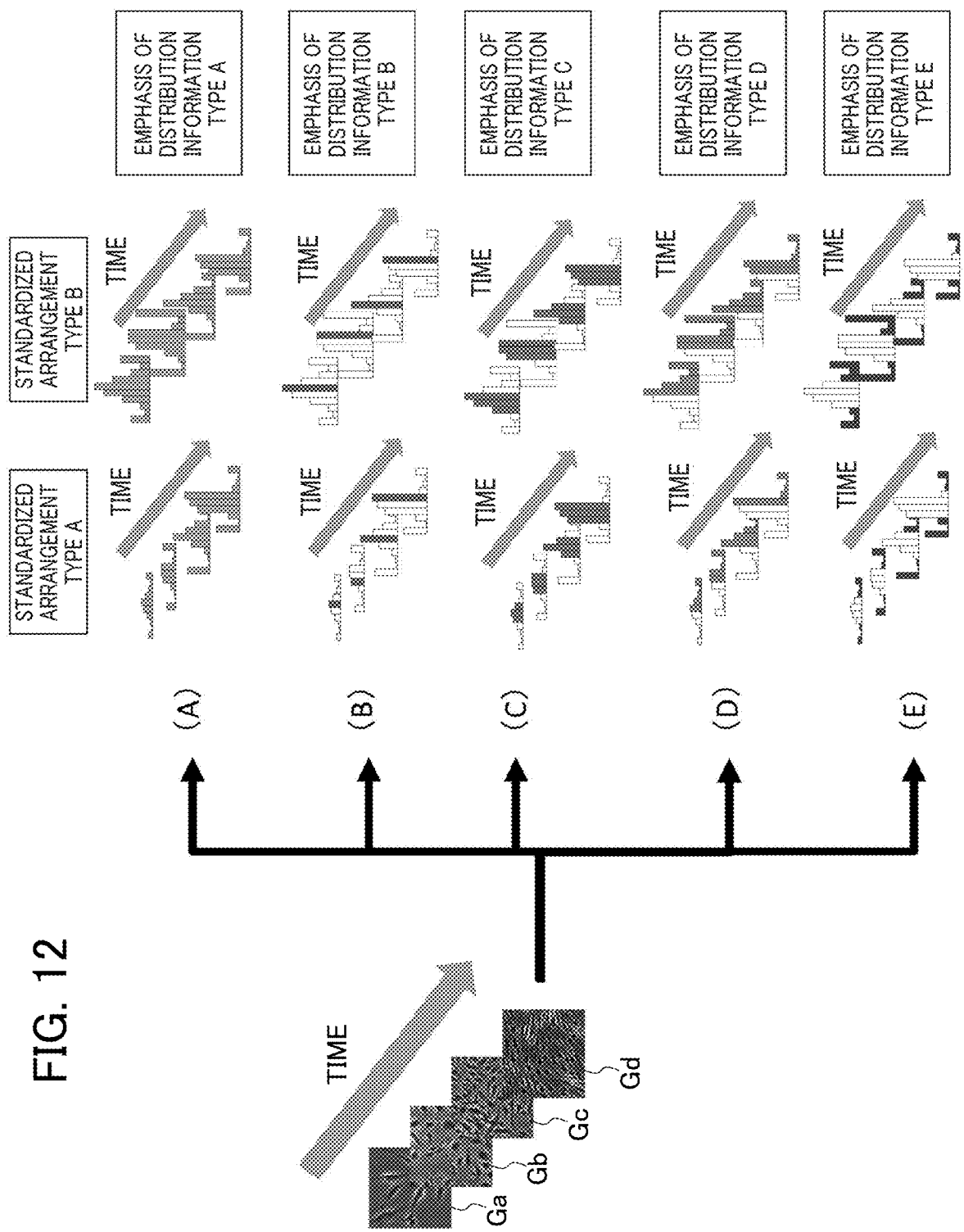
FIG. 12 shows various specific examples of approaches for processing population data in view of temporal changes.

FIG. 12 shows various specific examples of the approach for processing population data in view of temporal changes. It is noted that FIG. 10 described above represents examples based on cell images captured at three different timings while FIG. 12 in this case represents examples based on cell images Ga, Gb, Gc, and Gd at four different timings (24*h*, 48*h*, 72*h*, and 96*h*, respectively). However, the idea of each processing approach shown in FIG. 12 can also be applied to the examples in FIG. 10 in a similar way.

In the example of FIG. 12, first, a standardized arrangement type A and a standardized arrangement type B can be selectively used. The standardized arrangement type A represents a pattern in which absolute-value information as the numbers as a distribution (histogram) shown in FIG. 11 above (a histogram in which the numbers each obtained from the cell image G of FIG. 11 are used directly) is used. The standardized arrangement type B represents a pattern in which information standardized and normalized using the reference value within a data base shown in FIG. 11 above (a histogram in which the numbers each obtained from the cell image G of FIG. 11 are normalized) is used.

Figure 11:
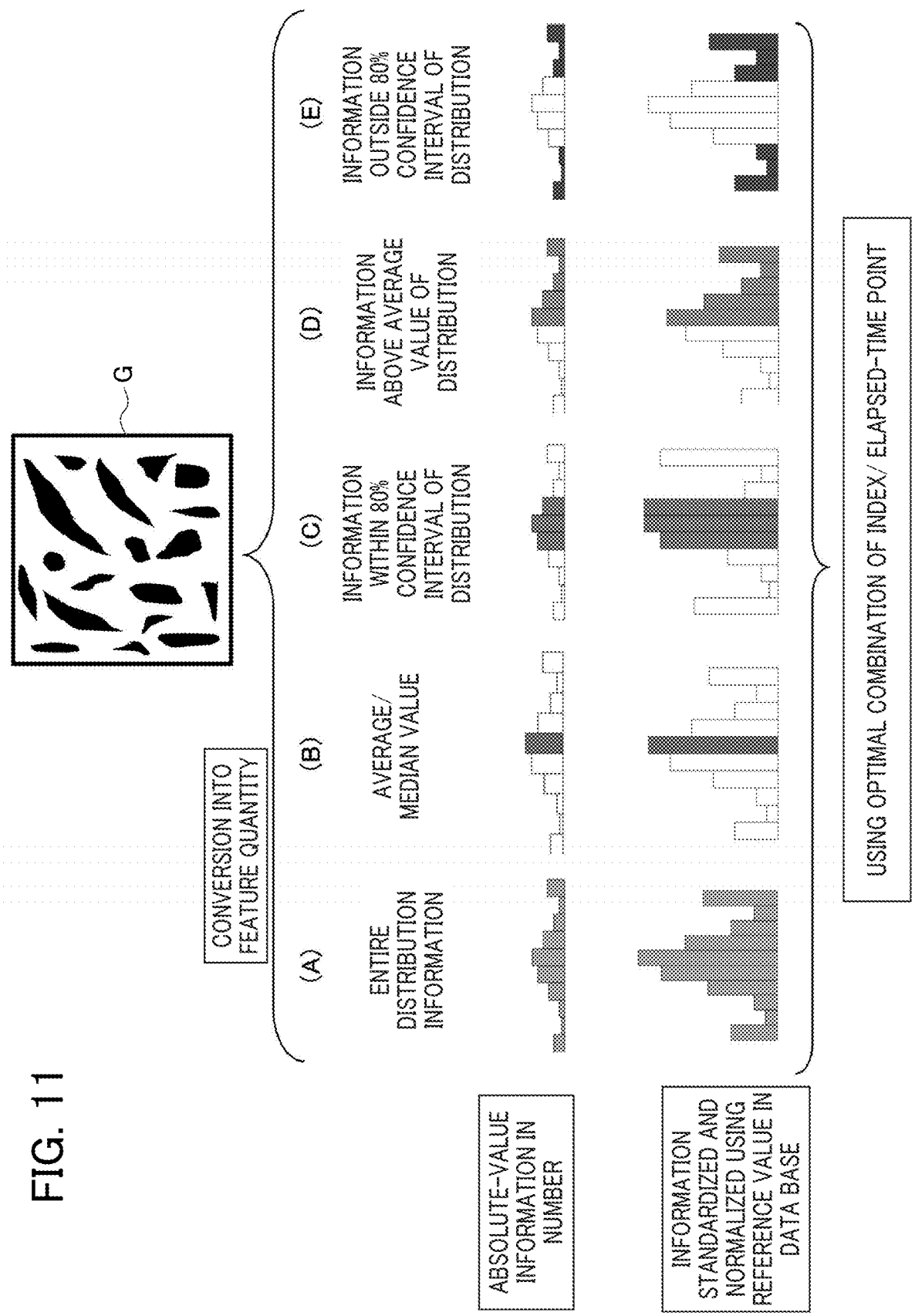
FIG. 11 shows various specific examples of patterns for emphasizing information contained in a distribution.

In FIG. 12, (A) schematically shows the feature-group information in view of temporal changes at the time points t1 to t5 when a pattern is used in which the whole distribution information of the histogram in FIG. 11(A) is used. In FIG. 12, (B) schematically shows the feature-group information in view of temporal changes at the time points t1 to t5 when a pattern is used in which the average/median value of the histogram in FIG. 11(B) is used. In FIG. 12, (C) schematically shows the feature-group information in view of temporal changes at the time points t1 to t5 when a pattern is used in which information within the 80% confidence interval of the histogram (distribution) in (C) of FIG. 11 is used. In FIG. 12, (D) schematically shows the feature-group information in view of temporal changes at the time points t1 to t5 when a pattern is used in which information above the average value in the histogram (distribution) of (D) of FIG. 11 is used. In FIG. 12, (E) schematically shows the feature-group information in view of temporal changes at the time points t1 to t5 when a pattern is used in which information outside the 80% confidence interval in the distribution of (E) of FIG. 11 is used.

Figure 13:
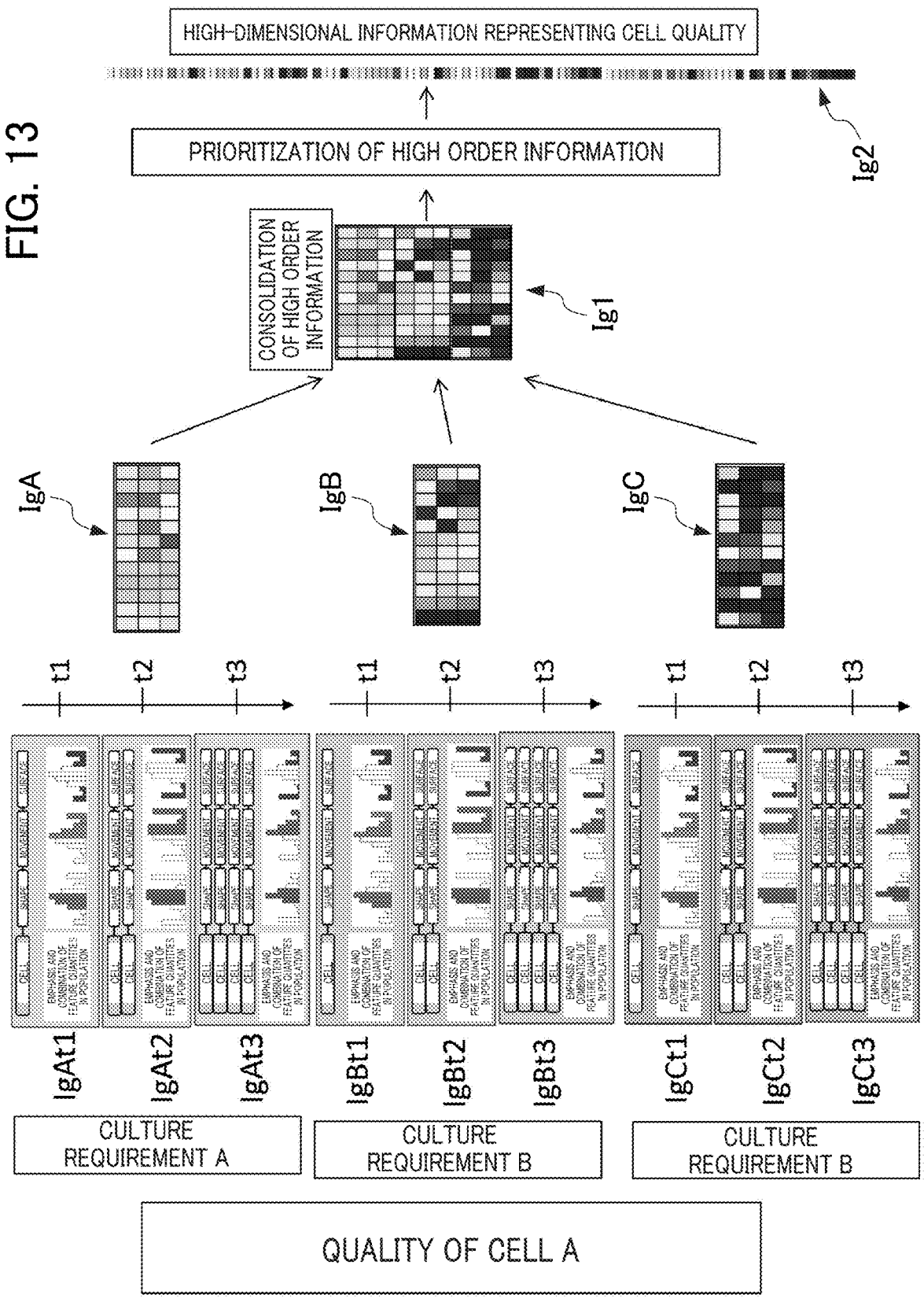
FIG. 13 shows various specific examples of approaches of processing population information in view of addition of heterogeneous information.

Next, the heterogeneous information adding unit 93 in FIG. 3 will be specifically described with reference to FIG. 13. FIG. 13 shows various specific examples of the approach for processing population information in view of addition of heterogeneous information. Addition of heterogeneous information means adding information which shows the relationship among a plurality of cell images captured at the same time under a plurality of requirements. That is, it means that the feature-group information obtained from each of a plurality of cell images captured at the same time under a plurality of requirements is processed (combined and/or rearranged) in view of changes in requirements.

FIG. 13 shows an example where cells of the same type A (in a three different containers) are cultured under a culture requirement A, a culture requirement B, or a culture requirement C.

That is, in the case of the culture requirement A, feature-group information IgAt1 at the time point t1, feature-group information IgAt2 at the time point t2, and feature-group information IgAt3 at the time point t3 are consolidated (processed) to construct feature-group information IgA. Similarly, in the case of the culture requirement B, feature-group information IgBt1 at the time point t1, feature-group information IgBt2 at the time point t2, and feature-group information IgBt3 at the time point t3 are consolidated (processed) to construct feature-group information IgB. In the case of the culture requirement C, feature-group information IgCt1 at the time point t1, feature-group information IgCt2 at the time point t2, and feature-group information IgCt3 at the time point t3 are consolidated (processed) to construct feature-group information IgcC.

Further, the feature-group information IgA for the culture requirement A, the feature-group information IgB for the culture requirement B, and the feature-group information IgC for the culture requirement C are consolidated into high order information to construct feature-group information Ig1. That is, this means that heterogeneous information in view of changes in requirements of the culture requirements is added. Further, contents in the high order information are prioritized to obtain feature-group information Ig2 as high dimensional information representing cell quality (in this case, the quality of the cell A).

As compared with the feature-group information at a predetermined time point under a predetermined requirement (for example, feature-group information IgAt1 at the time point t1 under the culture requirement A), the feature-group information Ig2 is considered as better information for indicating the quality of the cell A in that addition of heterogeneous information and temporal changes are taken into account.

It is noted that in the example of FIG. 13, processing (combination, rearrangement, and the like) in view of temporal changes is performed, and then heterogeneous information is added, but heterogeneous information may be added at each of the time points t1 to t3, and then processing such as consolidation (combination, rearrangement, and the like) in view of temporal changes may be performed. That is, the functional block diagram in FIG. 3 represents a functional block diagram of the latter case, but the order of arrangement of the temporal-change information adding unit 94 and the heterogeneous information adding unit 93 may be interchanged according to FIG. 13.

Figure 14:
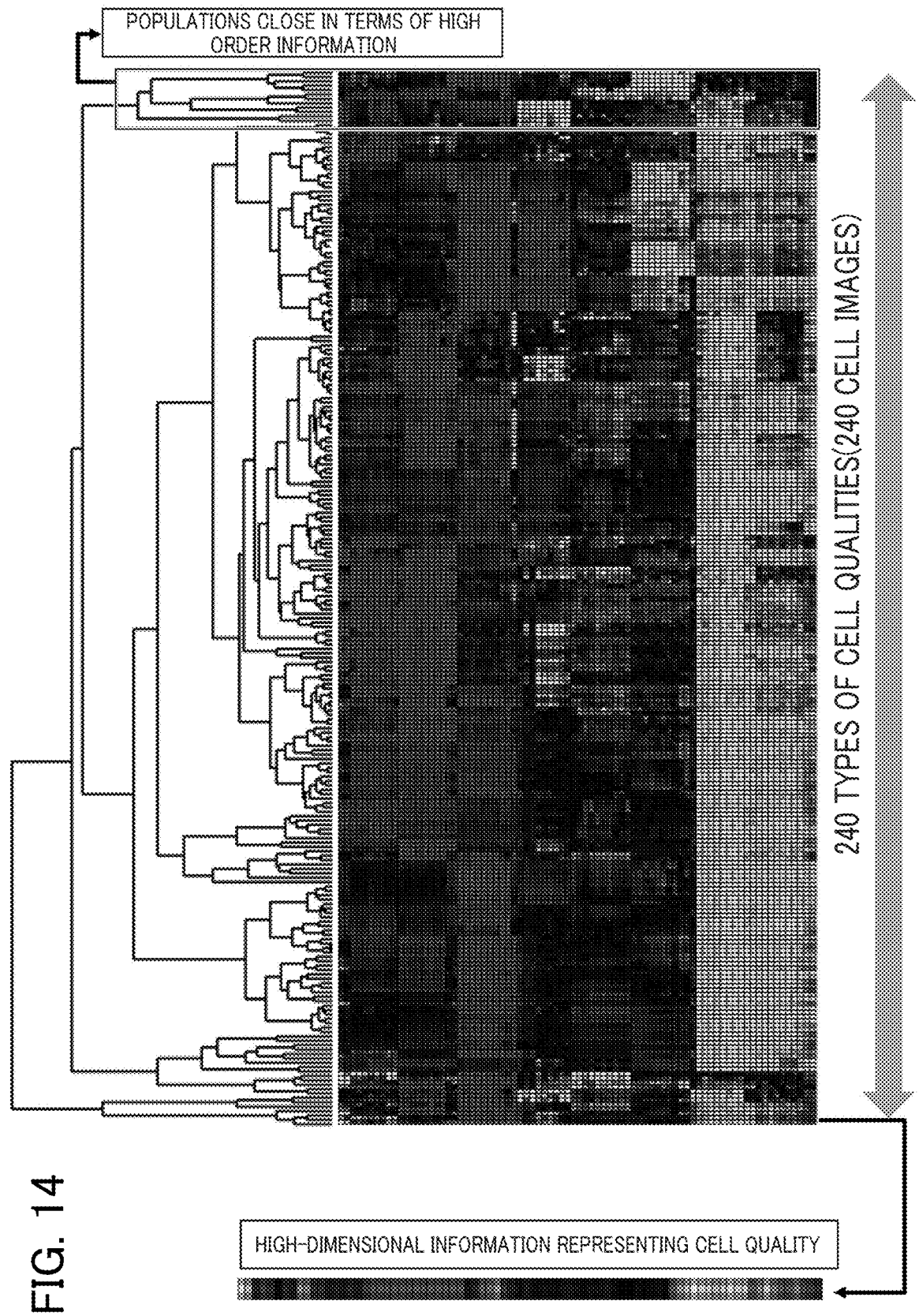
FIG. 14 shows an example of feature-group information processed in view of addition of heterogeneous information and temporal changes.

FIG. 14 shows a collection of 240 types of feature-group information representing cell quality processed in view of addition of heterogeneous information and temporal changes in this way, i.e., an example of feature-group information representing the quality of a plurality of cells. That is, in the example of FIG. 14, one predetermined column corresponds to feature-group information as high dimensional information representing one type of cell quality. It is noted that in the example of FIG. 14, items of high order information representing 240 types of cell qualities are not randomly listed, but arranged so that items of high order information having closer similarity are positioned more closely by means of clustering as described below. In this sense, a cladogram showing a closeness/remoteness in terms of similarity may be understood as a type of an analytical model. Based on the above understanding, the data in FIG. 14 may be considered as a group of sample data sets from which that analytical model is derived.

Hereinabove, a specific example of a series of steps of generating feature-group information is described with reference to FIGS. 10 to 14. Next, a series of steps up to generation of an analytical model by using a sample data set, the sample data set being generated from the above feature-group information, will be specifically described with reference to FIGS. 15 to 27.

Figure 15:
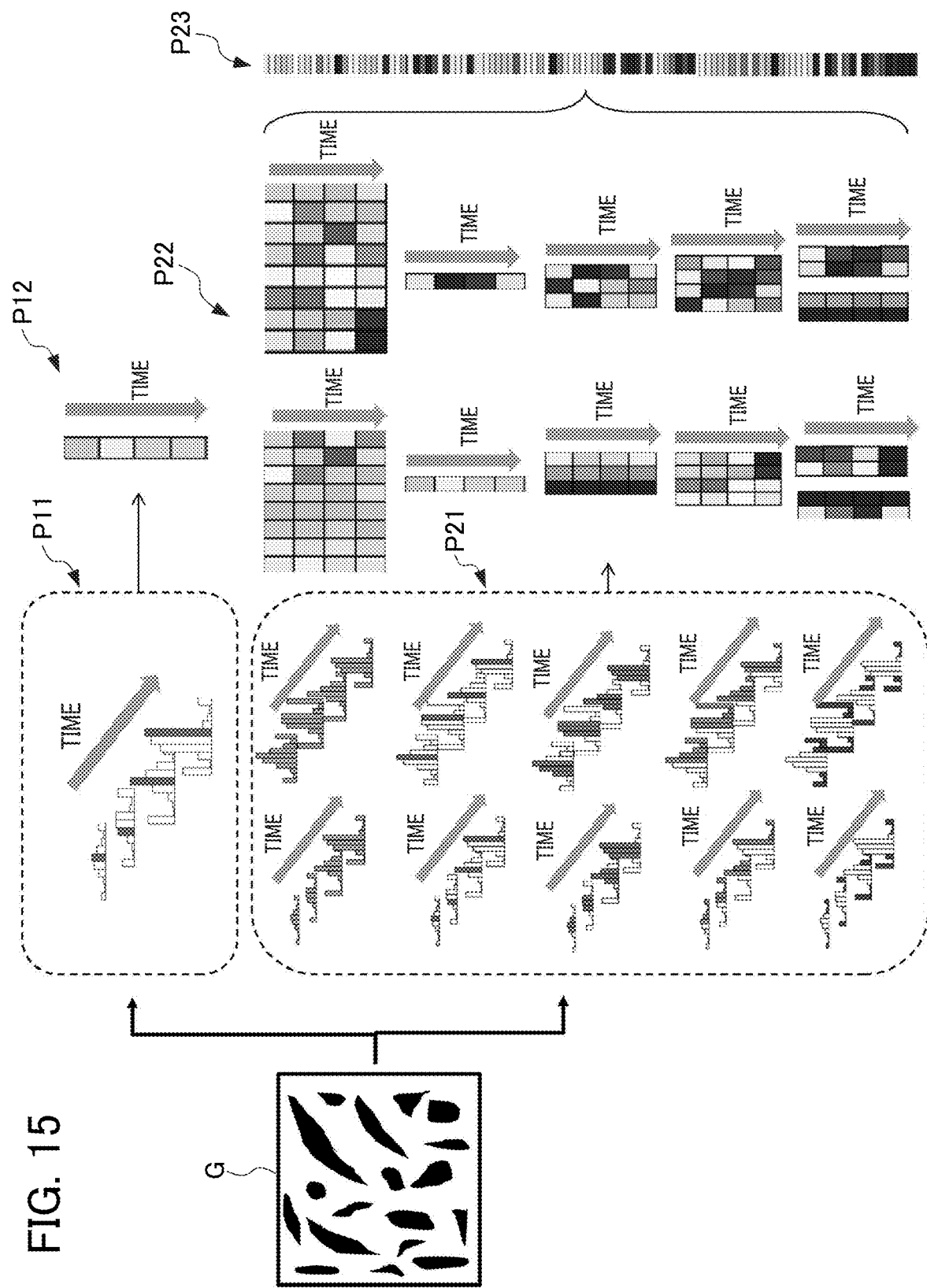
FIG. 15 shows differences between the conventional sample data set and the sample data set generated from the feature-group information according to the present embodiment.

FIG. 15 shows differences between the conventional sample data set and the sample data set generated from the feature-group information according to the present embodiment. The sample data set in the example of FIG. 15 is assumed to be used to generate an analytical model for predicting changes in cell quality.

The present inventors also used to use a sample data set P12 generated in view of temporal changes of a cell population in the past. However, the sample data set P12 was such that data sets P11 including the average value of cell morphology of a cell population at each time point which can be obtained the cell image G at each time point were simply listed in chronological order. In contrast, in the present embodiment, a collection P21 is obtained in which information for each of the patterns shown in FIG. 11 is extracted at each time point from a distribution (histogram) of cell morphology of a cell population. Feature-group information P22 is generated based on the above collection P21. Then, items of the feature-group information P22 are consolidated (rearranged and/or processed if needed) to obtain feature-group information P23 in a high dimensional form. Any number and any combination of data sets selected from the feature-group information P23 can be used as a sample data set.

Figure 16:
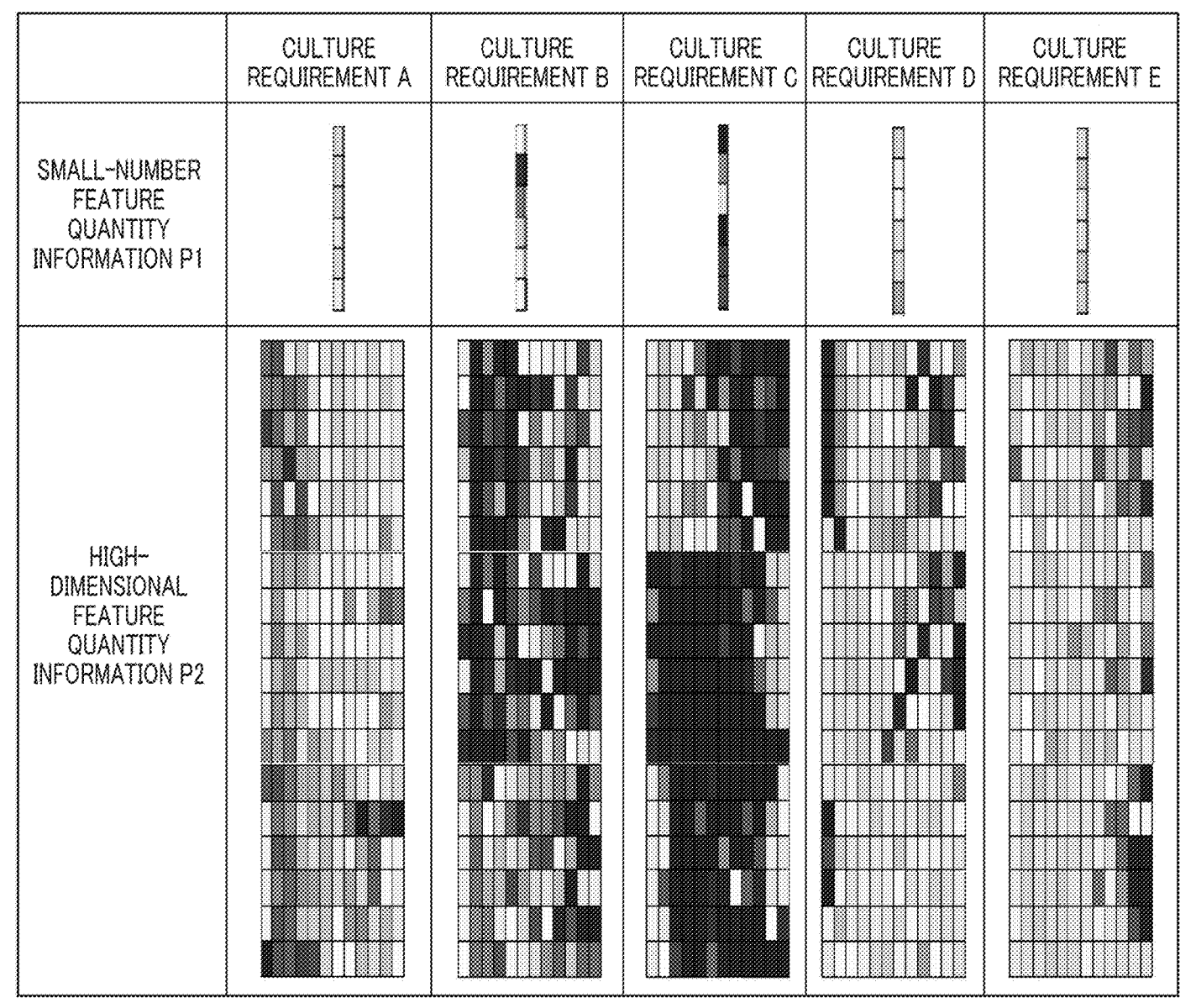

FIG. 16 shows an example of a sample data set used for generation of an analytical model for predicting changes in cell quality. In the example of FIG. 16, an example of the sample data set of each of qualities A to E. In FIG. 16, small-number feature quantity information P1 corresponds to the conventional sample data set P12 in FIG. 15. High-dimensional feature quantity information P2 corresponds to the feature-group information P23 in a high dimensional form according to the present embodiment in FIG. 15.

FIG. 17 shows predictive accuracy when changes in cell quality are predicted using the sample data set in FIG. 16. The term "average of cell morphology" refers to predictive accuracy when the small-number feature quantity information P1 in FIG. 16 (the conventional sample data set P12 in FIG. 15) is used. The term "standardized type A" refers to predictive accuracy when a portion of chronological information in a pattern where the whole distribution information in the histogram in (A) of FIG. 12 is extracted as a sample data set from the high-dimensional feature quantity information P2 in FIG. 16 (the feature-group information P23 in a high dimensional form in FIG. 15), and that sample data set is used. The term "standardized type B" refers to predictive accuracy when a portion of chronological information in a pattern where the average/median value of the histogram in (B) of FIG. 12 is extracted as a sample data set from the high-dimensional feature quantity information P2 in FIG. 16 (the feature-group information P23 in a high dimensional form in FIG. 15), and that sample data set is used. The term "standardized type C" refers to predictive accuracy when a portion of chronological information in a pattern where information within the 80% confidence interval of the histogram (distribution) in (C) of FIG. 12 is extracted as a sample data set from the high-dimensional feature quantity information P2 in FIG. 16 (the feature-group information P23 in a high dimensional form in FIG. 15), and that sample data set is used. The term "standardized type D" refers to predictive accuracy when a portion of chronological information in a pattern where information above the average value of the histogram (distribution) in (D) of FIG. 12 is extracted as a sample data set from the high-dimensional feature quantity information P2 in FIG. 16 (the feature-group information P23 in a high dimensional form in FIG. 15), and that sample data set is used. The term "standardized type E" refers to predictive accuracy when a portion of chronological information in a pattern where information outside the 80% confidence interval of the distribution in (E) of FIG. 12 is extracted as a sample data set from the high-dimensional feature quantity information P2 in FIG. 16 (the feature-group information P23 in a high dimensional form in FIG. 15), and that sample data set is used.

In the example of FIG. 17, the standardized type E shows the best predictive accuracy. That is, in the present embodiment, any number and any combination of items of information (including all, i.e., including the feature-group information P23 in a high dimensional form itself) selected from the feature-group information P23 in a high dimensional form can be used as a sample data set. Therefore, if a sample data set (the standardized type E in the example of FIG. 17) compatible with analysis items, analysis approaches, different requirements, and the like which are used for a predetermined analytical model is able to be found when generating that analytical model, the analytical model compatible with the analysis items, analysis approaches, different requirements, and the like can be generated using that sample data set.

FIG. 18 shows results from actual prediction of changes in cell quality by using an analytical model generated using the sample data set of the standardized type E shown in FIG. 17. In FIG. 18, labels of correct answers are shown in the row direction, and labels from analysis results are shown in the column direction. One combination of a predetermined cell type (quality) and a predetermined cell culture requirement are analyzed for 55 times, and results of the analyses are shown as square symbols. That is, prediction is successful when a place where a label of an analysis result agrees with a label of a correct answer is marked with a square symbol of an analysis result. As shown in FIG. 18, a highly accurate prediction is achieved.

Figure 19:
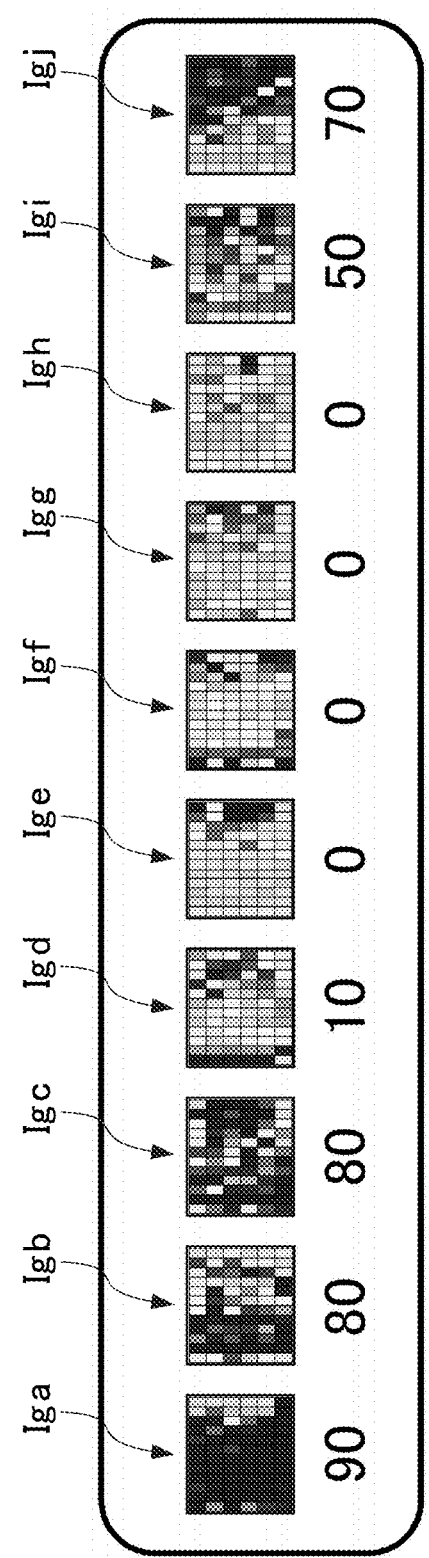
FIG. 19 shows an example of a plurality of sample data sets for generating a predetermined analytical model.
Figure 20:
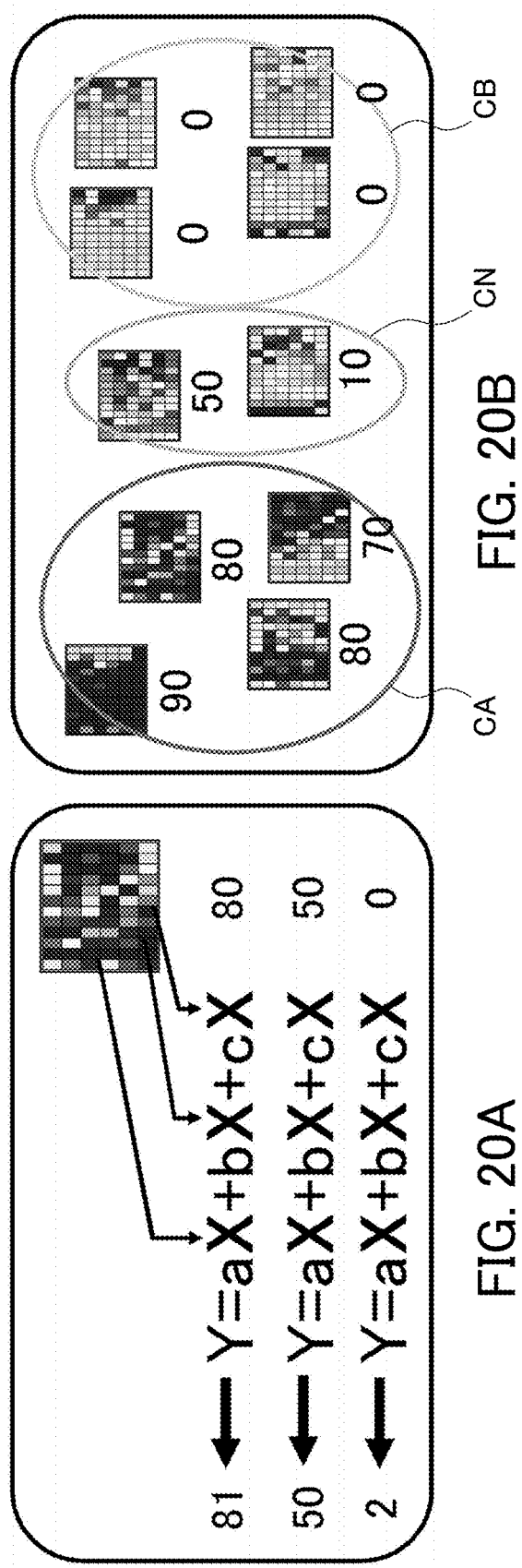
FIGS. 20A and 20B exemplify two approaches of generating a predetermined analytical model using the sample data sets in FIG. 19.

FIG. 19 shows an example of a plurality of sample data sets for use in generating a different predetermined analytical model than those in the examples described with reference to FIGS. 15 to 18. As described above, a plurality of sample data sets Iga to Igj are not image data but quantified data, and specifically represent multidimensional information including M types of parameters as elements. Here, a numerical value alone as an element in a sample data set also shows a morphological feature quantity and the like of a cell, and thus provides significant information. However, as a whole, the sample data sets Iga to Igj which are composed of combinations of these elements will provide more characteristic significant information as compared with other sample data sets. As understood from the example of FIG. 19, each of the elements is shown in a color and concentration corresponding to a value thereof, and a "figure" formed with a collection of the colors and concentrations of these elements provides significant information well indicating the features of each of the sample data sets Iga to Igj.

Here, an overall score is assumed be given to each of the plurality of sample data sets Iga to Igj in terms of a predetermined point of view. There is no particular limitation for the predetermined point of view, but a point of view is here assumed to be used in which cell types are categorized into the type A and the type B for the purpose of explanation. Then, it is also assumed that a larger number of features indicative of the type A are included (while a fewer number of features indicative of the type B are included) as the score approaches 100. Conversely, it is assumed that a larger number of features indicative of the type B are included (while a fewer number of features indicative of the type A are included) as the score approaches 0. That is, in the example of FIG. 19, the sample data set Iga has a scores of "90," which is the highest value, and thus represents data including a larger number of features indicative of the type A. Conversely, the sample data sets Ige to Igh each have a score of "0", which is the lowest value, and thus represent data including a larger number of features indicative of the type B. The sample data set Igi has a scores of "50", which is the median value, and thus represents data including both the features indicative of the type A and the features indicative of the type B.

It is noted that there is no particular limitation for the method of scoring each of a plurality of sample data sets Iga to Igj. For example, when corresponding evaluation-target information (known information obtained from different evaluations such as destructive tests) is stored in the cell evaluation DB 62 in FIG. 2 for each of the plurality of sample data sets Iga to Igj, an approach of scoring based on the above evaluation-target information may be used.

FIGS. 20A and 20B show two examples of the approach of generating a predetermined analytical model using the aforementioned sample data sets Iga to Igj shown in FIG. 19. Specifically, the examples in FIGS. 20A and 20B correspond to a case where an analytical model for categorizing cell types into type A and type B is generated as discussed in the above examples.

FIG. 20A shows an example in which an analytical model is generated by machine learning. In the example of FIG. 20A, an analytical-model generating unit 44 is configured to generate or renew a function (in the example of the figure, Y=aX+bX+cX) by performing machine learning using the plurality of sample data sets Iga to Igj, the function taking a value X of each of the M number of parameters in a sample data set as an input parameter, and outputting a score Y.

Here, it is assumed that feature-group information is generated from a cell image including an unknown type of cells as imaging subjects, and stored in the feature-group information DB 61 (FIG. 2). The evaluation-target information acquiring unit 46 acquires data having the same form as the sample data sets Iga to Igj (having the same M number of parameters) from the above feature-group information as evaluation-target information from the feature-group information DB 61.

In this case, in the analysis unit 47, the above function takes a value X of each of the M number of parameters in the evaluation-target information as an input parameter, and calculates a score Y for the evaluation-target information. A score Y for the above evaluation-target information close to 100 means that a cell corresponding to that evaluation-target information is analyzed to be likely of the type A. A score Y for the above evaluation-target information close to 0 means that a cell corresponding to that evaluation-target information is analyzed to be likely of the type B. A score Y for the above evaluation-target information having an intermediate value means that a cell corresponding to that evaluation-target information is analyzed to be inconclusive of whether it is of the type A or B.

That is, the "function which takes a value X of each of the M number of parameters in the evaluation-target information as an input parameter, and outputs a score Y for that evaluation-target information" is an example of an analytical model for categorizing cell types into the type A and the type B.

FIG. 20B shows an example in which an analytical model is generated by the clustering approach. In the example of FIG. 20B, the analytical-model generating unit 44 is configured to perform classification of the plurality of sample data sets Iga to Igj according to a predetermined algorithm. The types and numbers of classes resulted from classification depend on the plurality of sample data sets Iga to Igj and/or the predetermined algorithm, but here it is assumed that classification into three classes CA, CB, and CN is performed.

Here, it is also assumed that feature-group information is generated from a cell image including an unknown type of cells as imaging subjects, and stored in the feature-group information DB 61 (FIG. 2) as in the aforementioned example of FIG. 20A. The evaluation-target information acquiring unit 46 acquires data having the same form as the sample data sets Iga to Igj (having the same M number of parameters) from the above feature-group information as evaluation-target information from the feature-group information DB 61.

In this case, the analysis unit 47 classifies the above evaluation-target information into one of three classes CA, CB, and CN. When the above evaluation-target information is classified into the class CA, a cell corresponding to the above evaluation-target information is analyzed to be likely of the type A. When the above evaluation-target information is classified into the class CB, a cell corresponding to the above evaluation-target information is analyzed to be likely of the type B. Alternatively, when the above evaluation-target information is classified into the class CN, a cell corresponding to that evaluation-target information is analyzed to be inconclusive of whether it is of the type A or B.

That is, the "model for classifying evaluation-target information into one of three classes CA, CB, and CN" is an example of an analytical model for classifying cell types into the type A and the type B. Here, there is no particular limitation for the approach for classification, but for example, an approach may also be used in which similarity and others between each of the sample data sets Iga to Igj and evaluation-target information are each determined, and the evaluation-target information is classified based on that similarity and others. When the above approach is used, an analytical model is represented by "the plurality of sample data sets Iag to Ig, and the three classes CA, CB, and CN generated based on these."

Figure 21:
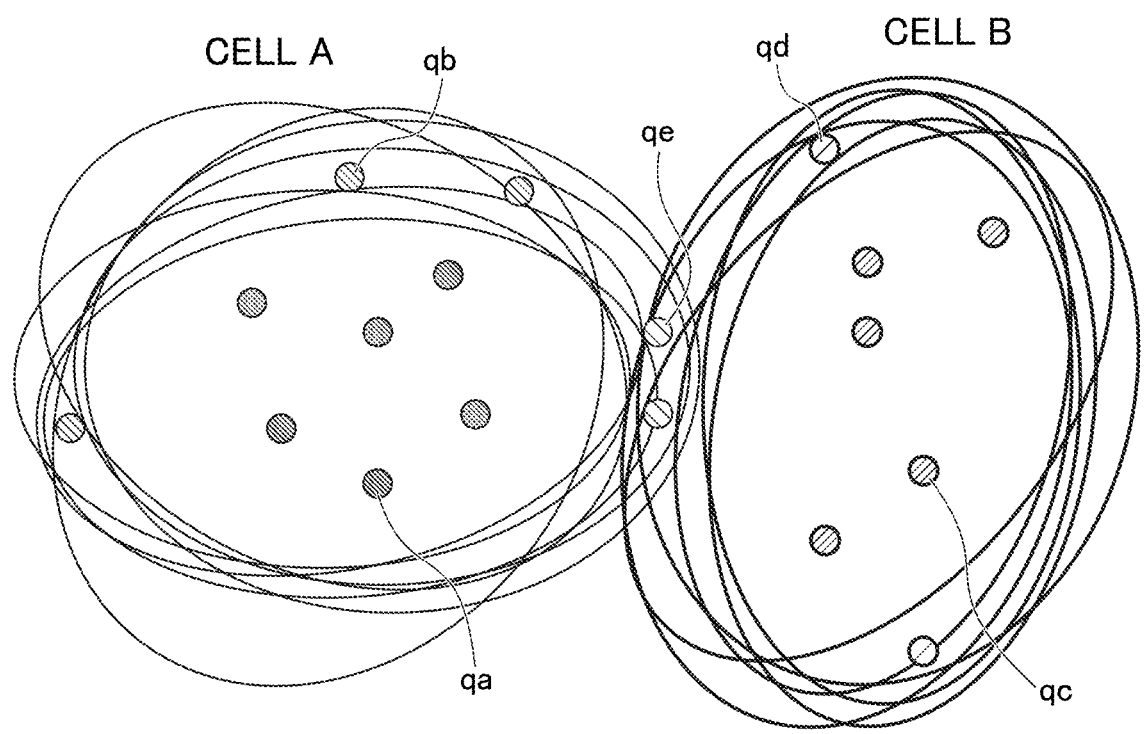
FIG. 21 shows an example of the representation form of an analytical model different from those described with reference to FIGS. 17 to 19.

It is noted that simple classification is described in FIG. 20B for the purpose of explanation. For example, an actual analytical model can be such that regions each based on each sample data set (elliptic regions each enclosed by the continuous line in FIG. 21) are overlaid as shown in FIG. 21. That is, FIG. 21 shows an example of the representation of an analytical model. Circles in this analytical model represent a sample data set or evaluation-target information.

Evaluation-target information qa is included within regions based on the sample data sets of all of the type A cells. Therefore, this means that a cell corresponding to the above evaluation-target information qa is analyzed to be very much likely of the type A. Evaluation-target information qb is included within regions based on the sample data sets of many of the type A cells. Therefore, this means that a cell corresponding to the above evaluation-target information qb is analyzed to be likely of the type A (however, less likely as compared to the evaluation-target information qa).

Evaluation-target information qc is included within regions based on the sample data sets of all of the type B cells. Therefore, this means that a cell corresponding to the above evaluation-target information qc is analyzed to be very much likely of the type B. Evaluation-target information qd is included within regions based on the sample data sets of many of the type B cells. Therefore, this means that a cell corresponding to the above evaluation-target information qd is analyzed to be likely of the type B (however, less likely as compared to the evaluation-target information qc).

Further, evaluation-target information qe is included in the overlapped region between the regions based on the sample data sets of the type A cells and the region based on the sample data sets of the type B cells. Therefore, this means that a cell corresponding to the evaluation-target information qe is analyzed to be inconclusive of whether it is of the type A or the type B.

As described above, the types of cell analysis significantly vary in terms of analysis items, analysis approaches, different requirements, and the like. Therefore, it is necessary to use a compatible sample data set and evaluation-target information per analysis item, analysis approach, requirement, and the like, and this can be achieved in the present embodiment. In other words, the sample data sets according to the present embodiment are not those simply obtained by directly extracting feature-group information, but the forms thereof (combinations of the number of parameters M and the types of parameters) can be altered so as to be compatible with analysis items, analysis approaches, different requirements, and the like. Then, an analytical model is generated from one or more sample data sets compatible with analysis items, analysis approaches, different requirements, and the like. Therefore, the resulting analytical model is also compatible with these analysis items, analysis approaches, different requirements, and the like. Further, when an unknown cell is analyzed, evaluation-target information having the same form as the sample data set is obtained as the data of that unknown cell by the evaluation-target information acquiring unit 46. That is, the evaluation-target information compatible with analysis items, analysis approaches, different requirements, and the like is obtained. In the analysis unit 47, analytical processing of the above unknown cell is performed using compatible evaluation-target information and a compatible analytical model (sample data set) per analysis item, analysis approach, requirement, and the like. In this way, the unknown cell can be easily and appropriately analyzed regardless of differences in analysis items, analysis approaches, different requirements, and the like.

Below, analytical processing by the analysis unit 47 and output information outputted from the output-information generating unit 48 will be further described in more detail.

Here, the sample data set is a collection of numerical values of M types of parameters (various feature parameters and/or various supplementary parameters), i.e., quantified information as described above. Therefore, an analytical model generated from a collection of a plurality of sample data sets is also easily expressed as quantified information. The evaluation-target information is also used for a cell to be analyzed. The above evaluation-target information is quantified information in the same form as the sample data set. Therefore, output information showing results of analytical processing using such evaluation-target information and such an analytical model (sample data set) can be easily formed in a form of enumeration (a list and others) of quantified information. However, a user who has requested cell analysis cannot easily recognize the analysis results and others when only the enumeration (a list and others) of such quantified information are presented. That is, the enumeration (a list and others) of quantified information alone is not sufficient as an output form presented to a user. Preferably, an easily recognizable visual form is also provided in combination. In order to achieve such an output form which can be easily recognized visually, the representation form of an analytical model is important. For example, the aforementioned representation form of an analytical model shown in FIG. 21, i.e., a form in which the analytical model is shown by overlaying regions based on each of the sample data sets (elliptic regions each enclosed by the continuous line in FIG. 21) is an example of an output form which can be easily recognized visually by a user.

Figure 22:
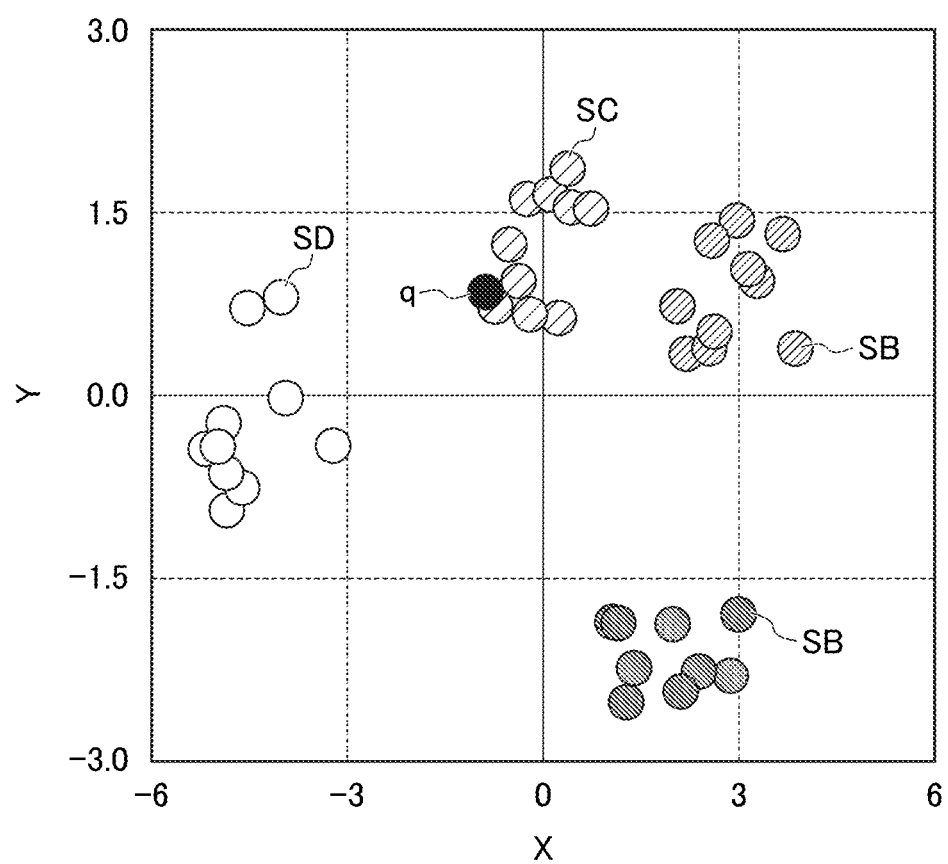
FIG. 22 shows an example of the representation form of an analytical model, which is different from that of the example in FIG. 21.

FIG. 22 shows an example of the representation form of an analytical model, which is different from that of the example in FIG. 21. In the example of FIG. 22, each sample data set is plotted as a point on a plane defined by predetermined two axes (X-axis, Y-axis). Each sample data set is categorized by color according to a group to which that sample data set belongs (categorized by different shadings in this figure). That is, an adjacent region where the sample data sets having the same color are found indicates a region of a group corresponding to that color. For example, in the fourth quadrant in this figure, the sample data sets of a first color (shading with the narrowest line interval in the figure) are concentrated near the sample data set SA. That is, the region of the fourth quadrant in this figure can be said to mainly belong to a region of a first group corresponding to the first color. Similarly, the region of the first quadrant in this figure (the adjacent region of a sample data set SB) can be said to mainly belong to a region of a second group corresponding to a second color (shading with the second narrowest line interval in the figure). An adjacent region at the positive side of the Y-axis (the adjacent region of a sample data set SC) can be said to mainly belong to a region of a third group corresponding to a third color (shading with the broadest interval in the figure). An adjacent region in the negative side of the X-axis (the adjacent region of a sample data set SD) can be said to mainly belong to a region of a fourth group corresponding to a fourth color (open symbols in the figure).

Further, evaluation-target information q can also be plotted on the plane on which the analytical model of FIG. 22 is shown. This enables a user to easily and immediately recognize in a visual manner that a cell corresponding to the evaluation-target information q likely belongs to the third group because the evaluation-target information q is located in the adjacent region at the positive side of the Y-axis.

Here, representation forms (a color, the shape of a symbol, and the like) of each plot of a sample data set or evaluation-target information may be altered in any way. Further, representation forms may be altered in any way according to analysis items, analysis approaches, different requirements, and the like as long as the sample data set is obtained from the same cell image group. For example, when representing an analytical model for categorizing the cell types, a representation form can be used in which each of plotting points is categorized by color for each of the types. Meanwhile, when representing an analytical model for determining the requirements of cells, another representation form can be used in which different symbol shapes are each assigned to plotting points according to the requirements. For example, a representation form can be used in which the symbol "○" is assigned to the requirement "good," and the symbol "▲" (triangle) is assigned to the requirement "fair," and the symbol "Δ" is assigned to the requirement "bad." In this case, a user can easily and immediately compare the types of cells by visually comparing the colors of plotting points, and can easily and immediately compare the requirements of cells by visually comparing the shapes of symbols in the plot.

Further, the X-axis and Y-axes are any variable axes, and can also be easily changed in response to a user's operation and the like. Specifically, a sample data set and evaluation-target information can be understood as multidimensional information in M dimensions including M types of parameters as elements, as described above. Therefore, plotting points on the plane in FIG. 22 can easily be determined by simply generating two elements X and Y based on the M types of parameters in the sample data set and/or the evaluation-target information. Here, there is no particular limitation for the X-axis and Y-axis, and any can be used. For example, any two-dimensional axes among the M dimensions in the sample data set and/or the evaluation-target information can also be directly used as the X-axis and Y-axis. Alternatively, for example, a new X-axis can be generated by combining any number of any dimensions selected from the M dimensions, and a new Y-axis can be independently generated by combining any number of any dimensions.

Figure 23:
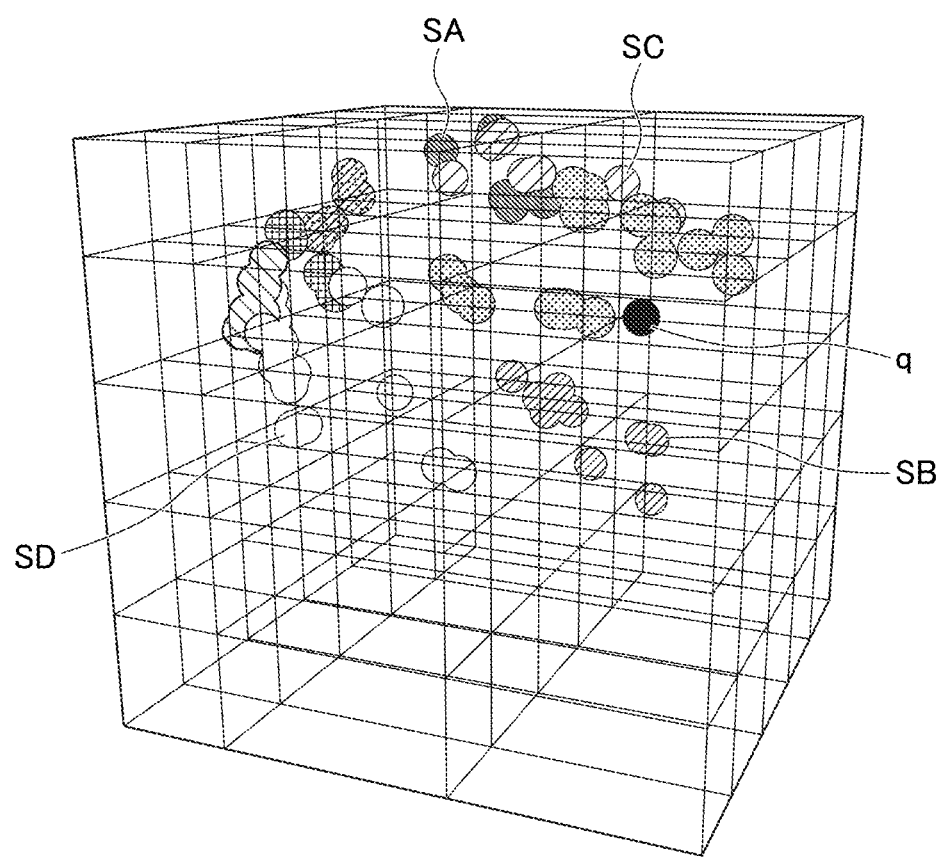
FIG. 23 shows an example of the representation form of an analytical model, which is different from the examples in FIGS. 21 and 22.

Further, the representation form of an analytical model does not necessarily need to be in a two-dimensional space, but may be in any dimensional space. For example, FIG. 23 shows an example of the representation form of an analytical model, which is different from the examples in FIGS. 21 and 22. That is, the analytical model in the example of FIG. 23 is represented in a three-dimensional space while the analytical models in the examples of FIG. 21 and FIG. 22 are represented in two-dimensional spaces. Here, the 3 axes defining a three-dimensional space can be any variable axes, and can easily be changed in response to a user's operation and the like exactly as in a case of the two-dimension. In principle, reduction in dimensions means that the amount of information is reduced (lacked) as compared with the original information. That is, all of the spaces in FIGS. 21 to 23 can be seen as projections or others of the M dimensional space consisting of the M types of parameters in a sample data (provided that M is 4 or more) in which some information is lacked as compared with the original sample data set. Therefore, the amount of lacked information is smaller in the three-dimensional space shown in FIG. 23 due to a larger number of dimensions as compared with the two-dimensional spaces shown in FIGS. 21 and 22. This enables a user to easily and immediately obtain a larger amount of information.

Further, the representation form of an analytical model does not necessarily need to be in a space where sample data sets and/or evaluation-target information are plotted as points. Any form may be used as long as the similarity of sample data sets and/or evaluation-target information can be visually recognized. Here, the similarity between two data sets can be represented, for example, as a distance between the two data sets. That is, data sets in a smaller distance are more similar. The aforementioned representations of an analytical model as shown in FIGS. 21 to 23 are first described because points in a space (a plot) is one of the representation forms in which such distance can be easily recognized visually. Next, another form of representation in which the similarity of sample data sets and/or evaluation-target information can be easily recognized visually will be described with reference to FIG. 24.

Figure 24:
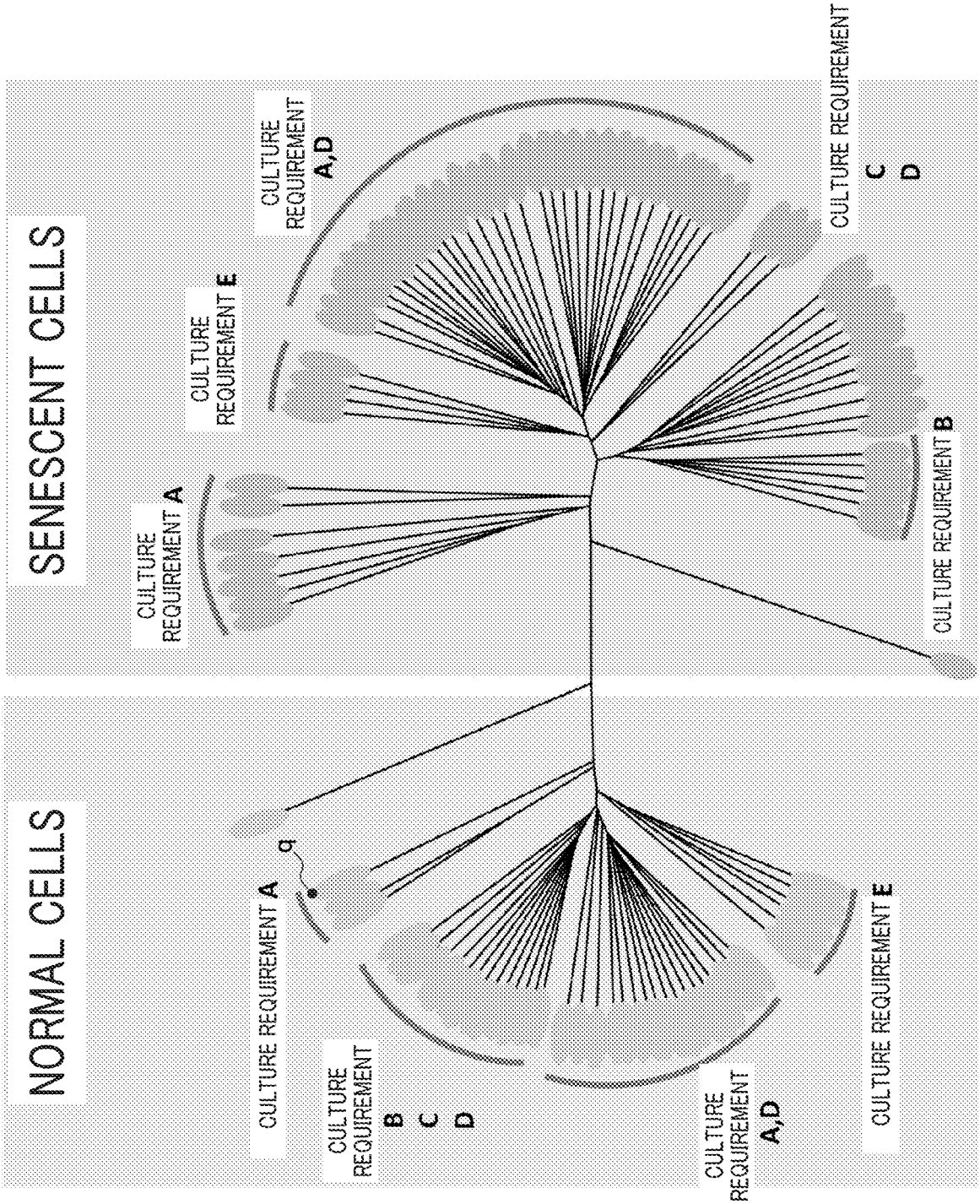
FIG. 24 shows an example of the representation form of an analytical model, which is different from the examples in FIGS. 21 and 23.

FIG. 24 shows an example of the representation form of an analytical model, which is different from the examples in FIGS. 21 to 23. In the example of FIG. 24, one line with an end represents one data set. That is, a collection of lines, the lines each corresponding to one of a plurality of sample data sets (hereinafter, a line is called a "branch," and the representation form as a collection of the branches is called "branched cladogram"), represents an analytical model generated using the plurality of sample data sets. A collection of closer branches in distance can be considered as one group because closer distance indicates stronger similarity as described above. Here, there are several branching points in a branch as shown in FIG. 22, and thus hierarchized groups can easily be created for each branching point as a unit in the branch. For example, in the example of FIG. 24, cells are categorized into normal cells and senescent cells at the first hierarchy level. Further, cells are categorized into a plurality of groups according to the differences in culture requirements in the corresponding second hierarchy level.

Further, the evaluation-target information q can also be plotted as one branch in the branched cladogram showing the analytical model in FIG. 24. By virtue of this, a user can easily and immediately recognize in a visual manner that a cell corresponding to the evaluation-target information q likely belongs to the group of the culture requirement A under the category of normal cells from the position where the branch of the evaluation-target information q is plotted in the branched cladogram.

Here, it should be noted that in the examples of FIGS. 21 to 24, the positional relationship between each sample data set (an overview of an analytical model) and the evaluation-target information is represented purely for the purpose of easy visual recognition by a user. That is, sample data sets and evaluation-target information are originally multidimensional information in M dimensions as described above. In the examples of FIGS. 21 to 24, spaces are represented where the M dimensions are reduced to two dimensions or three dimensions. That is, the analysis unit 47 in FIG. 2 actually does not calculate the similarity based on two-dimensional or three-dimensional data, but calculates the similarity between each of the sample data sets in M dimensions and the evaluation-target information in M dimensions. However, the outline of an approach of calculating the similarity between each of sample data sets and evaluation-target information will be described assuming M=3 for the purpose of explanation with reference to FIGS. 25 to 27. That is, it should be noted that the spaces in the examples of FIGS. 25 to 27 just happen to be in a form of M=3 dimensions, and they are inherently different from the three-dimensional space shown in FIG. 23.

Figure 25:
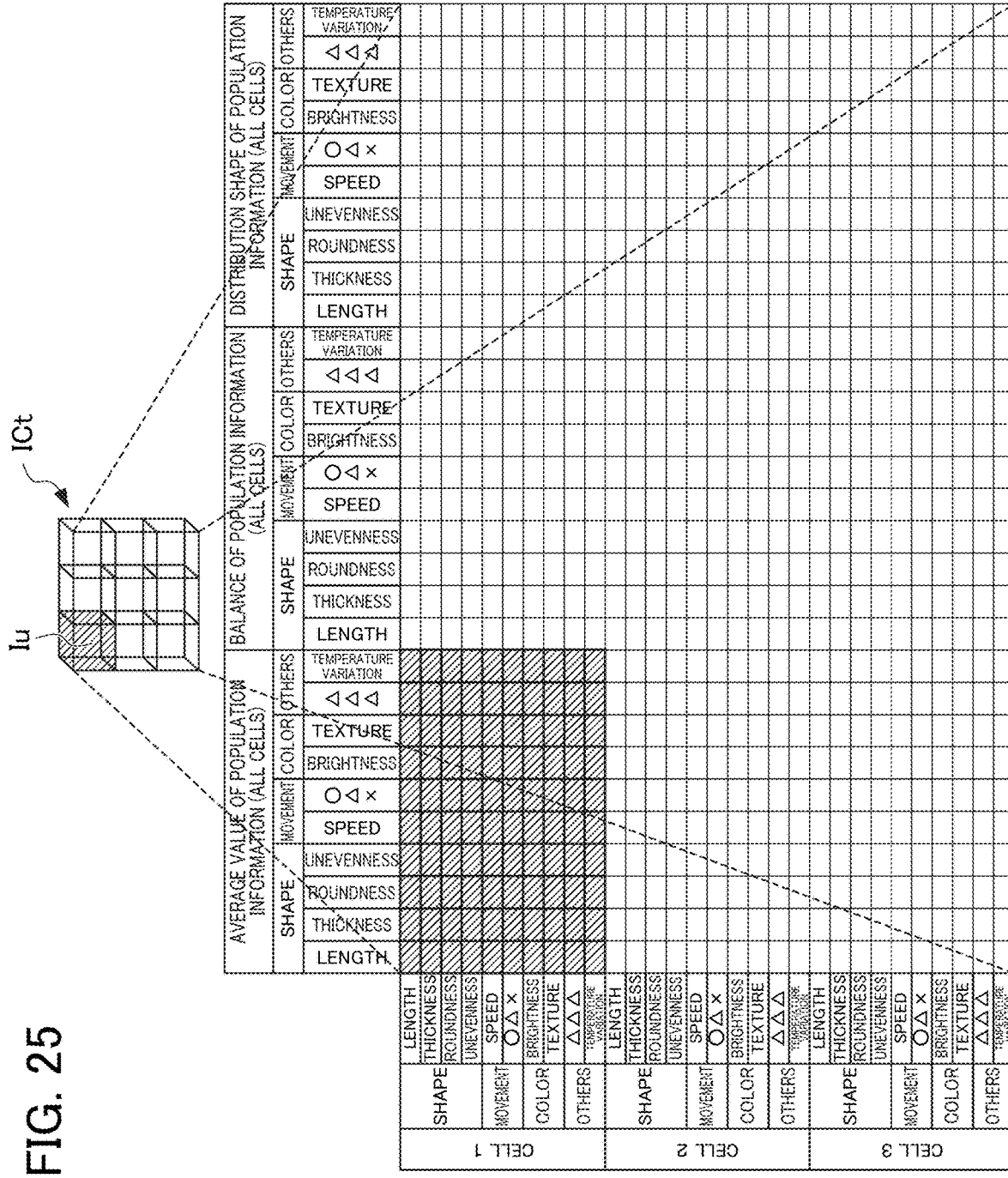
FIG. 25 shows an example of the structure of feature-group information, based on which a sample data set and evaluation-target information are generated.

FIG. 25 shows an example of the structure of the feature-group information as a basis of generating a sample data set and evaluation-target information. In FIG. 25, the items in the horizontal direction in the figure represent each element (feature parameter) in terms of a predetermined point of view (the average value, balance, and the shape of distribution) of a cell population of predetermined cells. That is, a value of each item in the horizontal direction is included as a value of each element in the feature-group information from which a sample data set is to be generated. The items in the vertical direction in the figure represent individual elements (feature parameters) for a predetermined cell. That is, a value of each item in the vertical direction in the figure is included as a value of each element in the feature-group information from which a sample data set is to be generated. It is noted that feature-group information ICt for a cell image captured at a predetermined time point including, as an imaging subject, a cell population of the same type cultured in a predetermined container is shown in the example of FIG. 25.

The above feature-group information ICt includes information in a two-dimensional space defined by the horizontal axis representing elements of the cell population in terms of predetermined points of view and the vertical axis representing individual elements of a cell. Here, unit information Iu is generated based on the group of values (items of information in the vertical axis) of the feature parameters of a predetermined cell at a predetermined time point for the predetermined cell, and the group of values (items of information in the horizontal axis) of the feature parameters of a cell population containing the above predetermined cell in terms of the predetermined points of view. When the unit information Iu described above is used, positioning of a predetermined cell in the cell population in terms of a predetermined point of view at a predetermined time point can be understood. For example, from the unit information Iu which is shaded and located at the upper left in FIG. 25, comparison of a value of each feature parameter (for example, length) of a cell 1 (the predetermined cell) can be made in terms of the average value of each feature parameter of the cell population (for example, the average value of lengths in the entire population).

Figure 26:
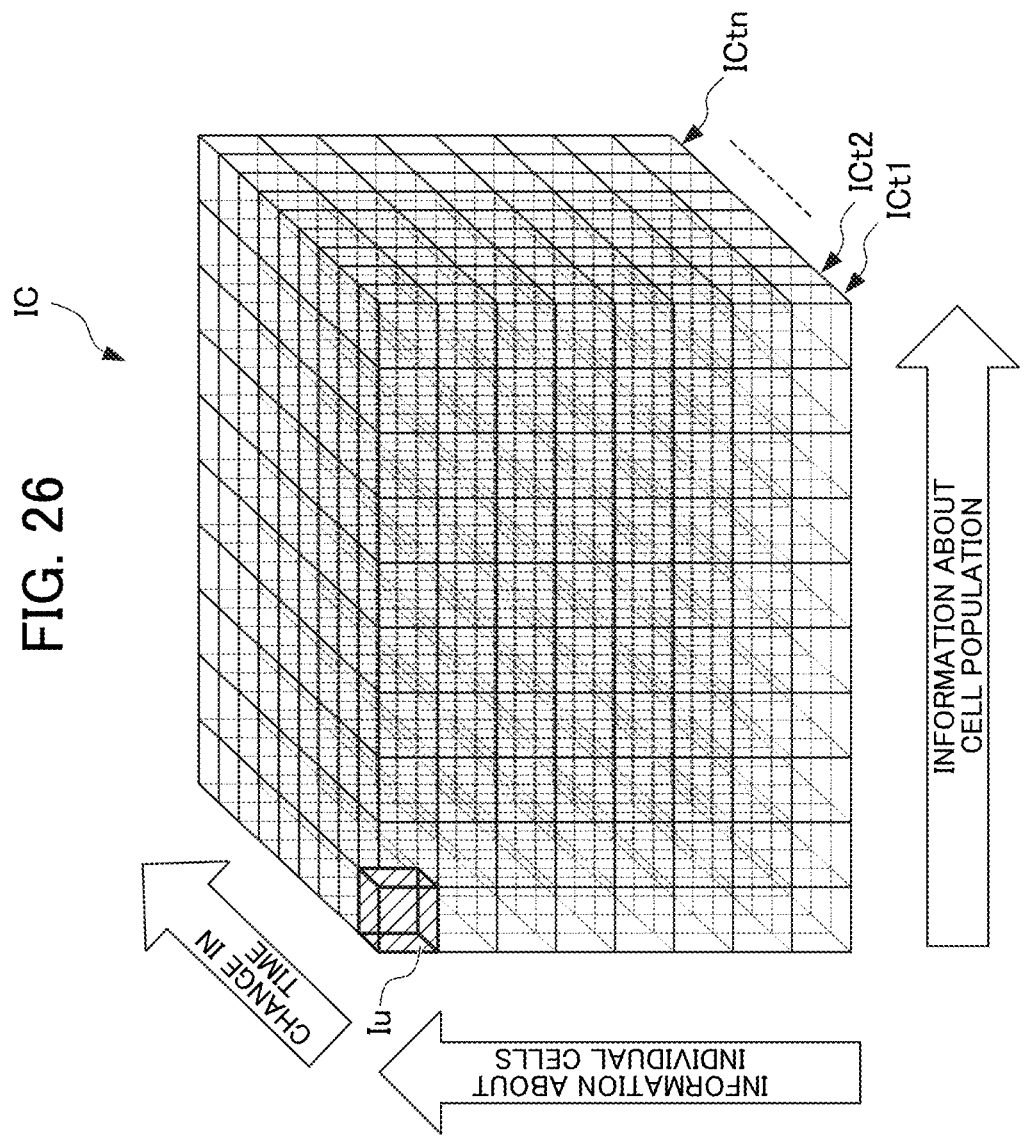
FIG. 26 shows an example of the structure of the feature-group information generated in view of temporal changes in FIG. 25.

Here, for a cell population contained in the same container, a cell image is assumed to be captured for n times in the time direction (at each of the time points t1 to tn). In this case, the feature-group information ICt in FIG. 25 shows an appearance of a cell image of the cell population contained in the same container captured at a predetermined time tk (k is an integer having a value in a range of 1 to n). That is, as shown in FIG. 26, n items of feature-group information ICt1 to ICtn are obtained which represent the appearances of cell images of the cell population contained in the same container each captured at each of the time points t1 to tn. The n items of feature-group information ICt1 to ICtn are sequentially layered in the time direction to form feature-group information IC.

That is, the feature-group information IC includes items of information in which one of more items of unit information Iu are arranged in a three-dimensional space defined by the vertical axis representing individual information of a cell, the horizontal axis representing information of a cell population in terms of predetermined points of view, and the depth axis representing temporal changes. Here, there is no particular limitation for the form of the unit information Iu, but it is assumed to be in a form of binary values of "significant information (1)" or "insignificant information (0)" for the purpose of explanation. For example, when a predetermined analysis item such as categorization of cell types and the like is used, a value supportive of categorizing cell types may be included in the values of elements (various feature parameters) in each unit information Iu. If such a value is included, the "significant information (1)" is assigned to that unit information Iu. On the other hand, if the value supportive of categorizing cell types is not included, the "insignificant information (0)" is assigned to that unit information Iu. That is, even the cells of the same type included in the same container can be either the "significant information (1)" or the "insignificant information (0)" depending on the features of individual cells, the positioning within the cell population in terms of a predetermined point of view, the temporal changes, and the like.

Figure 27:
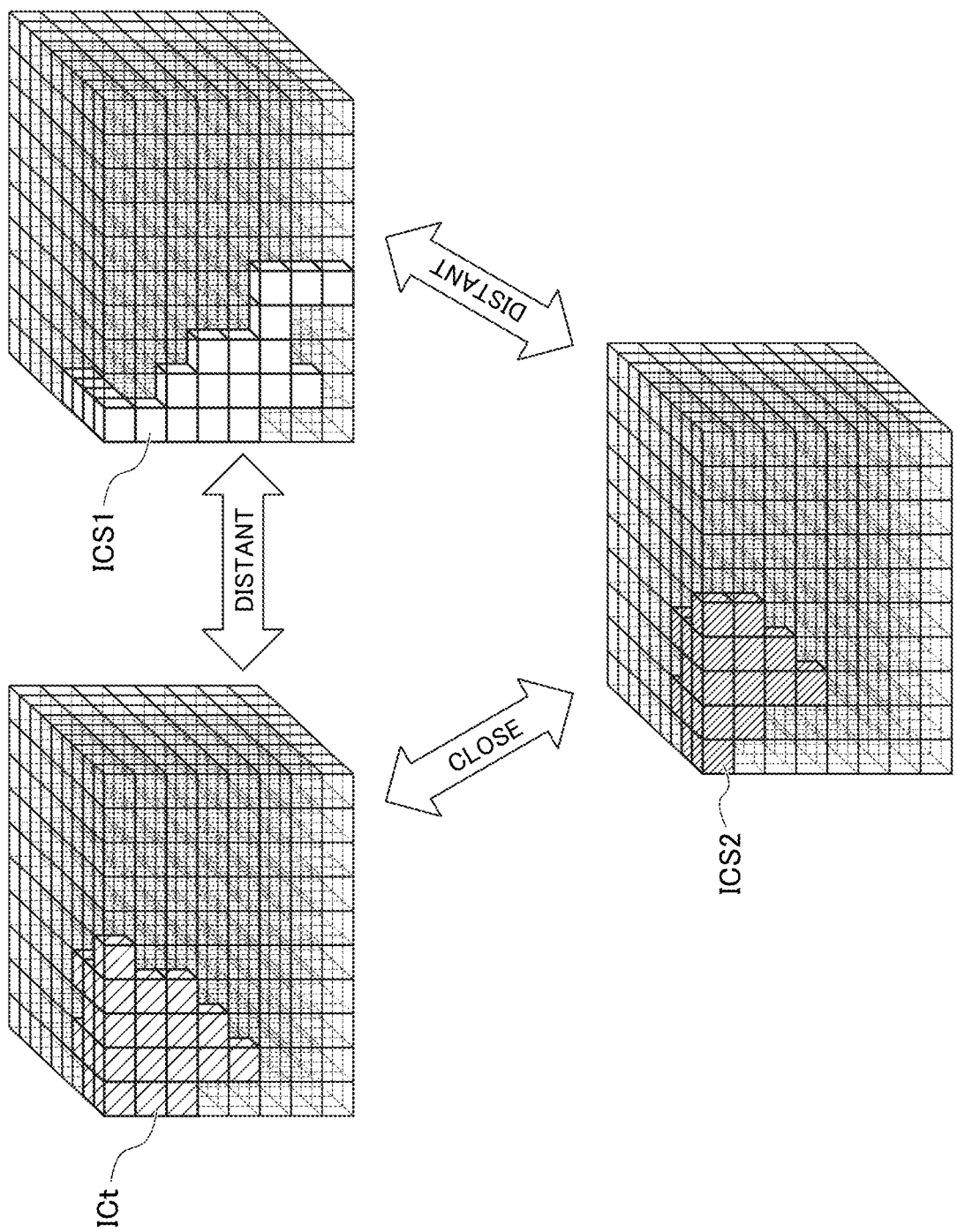
FIG. 27 illustrates an example of an approach of comparing a sample data set and evaluation-target information using feature-group information having a structure shown in FIG. 26.

In the analytical-model generating unit 44 (FIG. 2), a single item of feature-group information IC is generated using, as one unit, the n number of cell images of the same type of cells contained in the same container captured at each of the time points t1 to tn, and only the unit information Iu which can be used as the "significant information (1)" is extracted from that one unit of the feature-group information IC. In the analytical-model generating unit 44, a collection of multiple items of unit information Iu extracted in this way is generated as a sample data set. Here, the unit information Iu can be represented as positional coordinates on a three-dimensional space in which the feature-group information IC is to be constructed as shown in FIG. 26, i.e., can be represented as three-dimensional information. That is, as shown in FIG. 27, a collection of unit information Iu (the unit information Iu which is shaded in FIG. 27) as "significant information (1)" each arranged in the three-dimensional space in which the feature-group information Ic is to be constructed will serve a sample data set. For example, a sample data set ICS1 at the upper right panel in FIG. 27 is assumed to show the type A. Further, for example, a sample data set ICS2 at the lower center panel in FIG. 27 is assumed to show the type B. That is, a collection of these sample data sets ICS1, ICS2, and the like will serve as an analytical model for categorizing cell types into the type A and the type B.

In other words, the unit information Iu is based on the feature-group information at least including 10 elements (feature parameters) of a predetermined single cell and 10 elements (feature parameters) of a cell population in terms of a predetermined point of view. Each of these elements is rearranged in terms of whether it is "significant information (1)" or "insignificant information (0)," and each unit information Iu determined as "significant information (1)" is represented at a positional coordinate in a three-dimensional space where the feature-group information IC is to be constructed, i.e., represented in terms of three axial elements. That is, this is equivalent to a case in which a three-dimensional sample data set is extracted from feature-group information having at least 20 or more dimensions.

Here, it is assumed that the n number of cell images of an unknown type of a cell population contained in the same container captured at each of the time points t1 to tn is also treated as one unit, and this one unit is given as an analysis target. In this case, the evaluation-target information acquiring unit 46 acquires the data constructed in accordance with the completely same approach as used for aforementioned sample data sets ICS1 and ICS2 as the evaluation-target information Ict shown in the upper left panel in FIG. 27.

In the analysis unit 47, the similarity is determined by calculating the distance between the evaluation-target information Ict and the sample data set ICS1. Similarly, in the analysis unit 47, the similarity is determined by calculating the distance between the evaluation-target information Ict and the sample data set ICS2. There is no particular limitation for the approach of calculating distance, but for example, approaches based on Euclid distance and Mahalanobis distance can be used. In the example of FIG. 27, the distance between the evaluation-target information Ict and the sample data set ICS2 is smaller than the distance between the evaluation-target information Ict and the sample data set ICS1. Therefore, the evaluation-target information Ict is determined to be similar to the sample data set ICS2. That is, this means that a cell corresponding to the evaluation-target information Ict is analyzed to be likely of the type B to which the sample data set ICS2 belongs.

The output-information generating unit 48 generates output information including results from analysis performed by the analysis unit 47 as described above and the evaluation-target information acquired by the evaluation-target information acquiring unit 46, and outputs it to the output unit 16 and/or the external apparatus 81.

Figure 28:
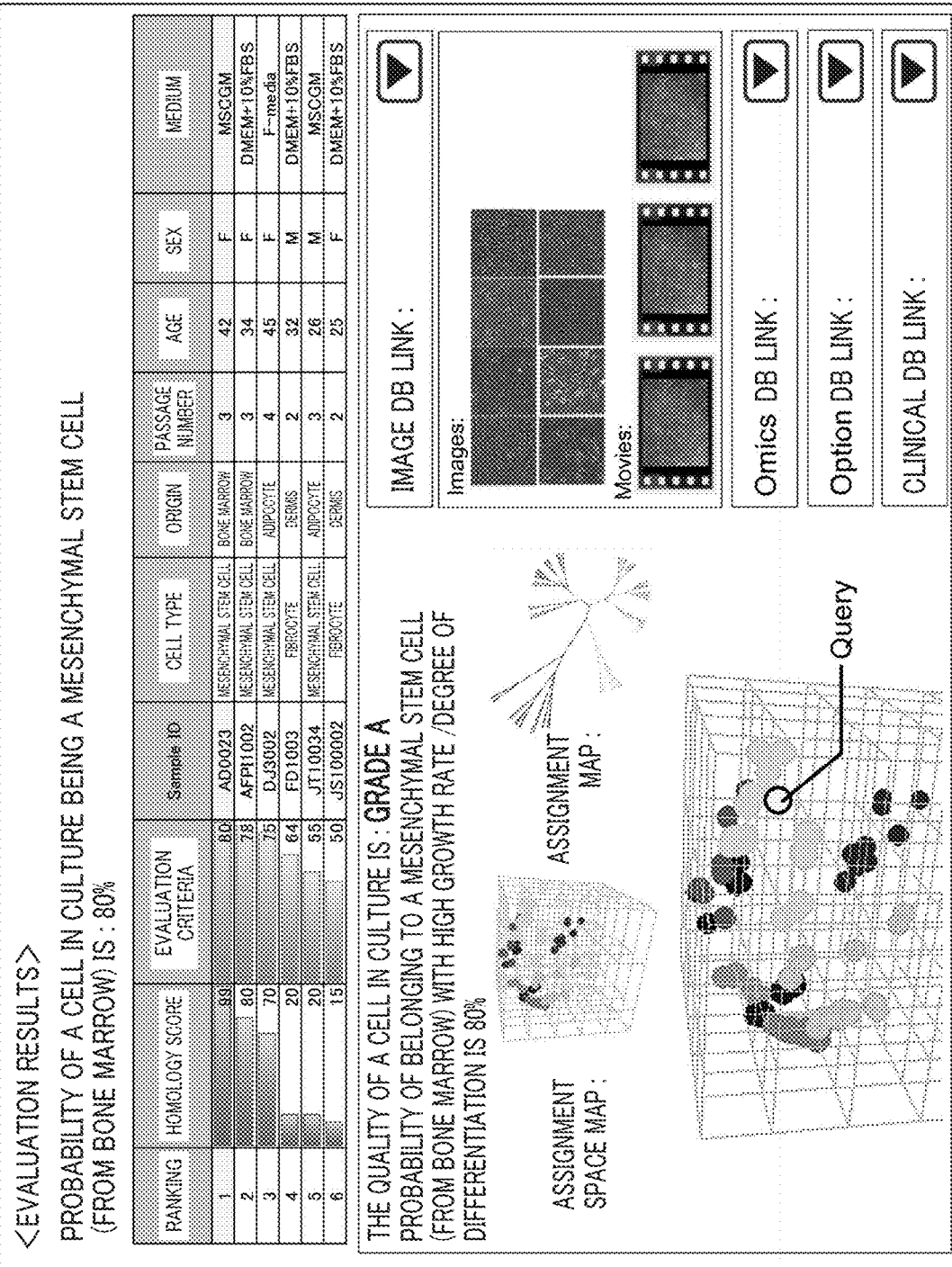
FIG. 28 shows an example of a screen in which output information is displayed.

FIG. 28 shows an example of a screen which displays output information. In a screen G0 shown in the example of FIG. 28, analysis results such as types of cells (cells in culture) as analysis targets are displayed not only as lists of numerical values but also as an assignment space map and an assignment map which can be easily recognized in a visual manner.

In the assignment space map, various sample data sets and the evaluation-target information representing a cell (a cell in culture) as an analysis target are plotted as points in a three-dimensional space defined by arbitrary axes as described above with reference to FIG. 23. In the example of FIG. 28, a plotting point (circle) indicated as "Query" represents evaluation-target information.

In the screen G0, an assignment map may be displayed instead of the assignment space map as shown in FIG. 29. The assignment map is a branched cladogram in which each various sample data set is considered as one branch (line), and a closer branch means strong similarly as described above with reference to FIG. 23. In the example of FIG. 27, a plotting point (circle) indicated as "Query" represents evaluation-target information. This enables a user to immediately and easily recognize analysis results (how likely a cell belongs to what type, and others) of cells as evaluation targets in a visual manner. It is convenient.

As another characteristic point, the classification results are presented as probability (likelihood). That is, an assignment to the type A is not provided in a conclusive manner, but shown in the terms of the similarity with a sample of the type A (probability of belonging to the type A). This enables a user to obtain more accurate and more valuable information. For example, it is assumed that a cell is conclusively determined as the type A merely based on a slightly higher likelihood when there is a possibility of either the type A or the type B as described above. In this case, the analysis result provided is wrong if the cell actually turns out to be of type B. This may be responsible for a future problem which may occur to the user. In contrast, a user is provided with a possibility of either the type A or the type B in the present embodiment. This allows the user to also consider the possibility of type B, enabling the user to easily manage a case where the cell actually turns out to be of type B.

As yet another characteristic point, not only an "evaluated probability" of types (cell type) but also a "homology score" are provided. That is, an analysis approach of categorizing cell types is mainly described above for the purpose of explanation, but the similarity in terms of "origins" can also be outputted by analyzing and comparing a sample data set with evaluation-target information in a similar fashion. The above similarity in terms of "origins" is a homology score. For example, when comparing sample data sets which are second and third in the rank, the evaluated probability (the similarity in terms of types) of the sample data set ranked in the second place is "78" while that of the sample data set ranked in the third place is "75." They are not significantly different. However, the homology score (the similarity in terms of origins) of the sample data set ranked in the second place is "80" while that of the sample data set ranked in the third place is "70." The difference between them is large. Therefore, a user can easily determine to some extent that the "origin" of the cell as analysis target is not "adipocyte" but "bone marrow."

An embodiment of the present invention is described hereinabove, but the present invention shall not be limited to the aforementioned embodiment. Modifications and improvements within the range where an object of the present invention can be achieved shall be included within the present invention.

In other words, there is no particular limitation for the embodiment of a cell-analyzing data generating apparatus to which the present invention can be applied as long as the apparatus has the following configuration. That is, the aforementioned cell analysis apparatus 1 is an example of the cell-analyzing data generating apparatus.

That is, the cell-analyzing data generating to which the present invention can be applied includes: a feature-group information generating means (for example, the feature-group information generating unit 42 in FIG. 2) configured to generate, as feature-group information, information including values of N types of feature parameters (wherein N represents an integer having a value of 1 or more) about a morphological feature of a single cell of a plurality of cells or a morphological feature of a cell population based on data of one or more cell images included in a unit, the one or more cell images in the unit being selected from cell images capturing the cell population including the cells as an imaging subject in accordance with a predetermined requirement; and an information acquiring means (for example, the analytical-model generating unit 44 and/or the evaluation-target information acquiring unit 46) configured to acquire, as information for use in performing predetermined cell analysis, information including values of M types (wherein M is an integer having a value independent of N) of parameters (for example, a sample data set for generating an analytical model, evaluation-target information of a target to be analyzed using that analytical model) based on at least one of the N types of feature parameters included in the feature-group information. Thereby, compatible cell-analyzing information can be generated per different analytical model.

Further, there is no particular limitation for the embodiment of a cell-analysis model generating apparatus to which the present invention can be applied as long as the apparatus has the following configuration. That is, the aforementioned cell analysis apparatus 1 is an example of the cell-analysis model generating apparatus.

That is, the cell-analysis model generating apparatus to which the present invention can be applied includes: an information acquiring means (for example, an information acquiring function of the analytical-model generating unit 44 in FIG. 2) configured to acquire, as one or more sample data sets, information including values of M types (wherein M is an integer having a value independent of N) of parameters based on at least one of N types of feature parameters included in feature-group information about a cell image for use as a sample in a case where the feature-group information is retained (for example, in the feature-group information DB 61 in FIG. 2), the feature-group information being generated from data of one or more cell images included in a unit, the one or more cell images in the unit being selected from cell images capturing a cell population including a plurality of cells as an imaging subject in accordance with a predetermined requirement, and the feature-group information including values of the N types of feature parameters (wherein N represents an integer having a value of 1 or more) about a morphological feature of a single cell of the cells or a morphological feature of the cell population; and a model generating means (for example, model generating function of the analytical-model generating unit 44 in FIG. 2) configured to generate an analytical model for performing cell analysis using the one or more sample data sets acquired, Thereby, a compatible analytical model can be efficiently generated for each of analysis items, analysis approaches, and different requirements.

Further, there is no particular limitation for the embodiment of a cell analysis apparatus to which the present invention can be applied as long as the apparatus has the following configuration. That is, the aforementioned cell analysis apparatus 1 is an example of the analysis apparatus.

That is, the cell analysis apparatus to which the present invention can be applied is a cell analysis apparatus for performing analytical processing on a cell using an analytical model generated from one or more sample data sets, the apparatus including: an acquisition means (for example, evaluation-target information acquiring unit 46 in FIG. 2) configured to acquire data about a cell image to be subjected to analytical evaluation as evaluation-target information, the data being in the same form as the one or more sample data sets; and an analysis means (for example, analysis unit 47 in FIG. 2) configured to perform analytical processing on the cell image corresponding to the evaluation-target information based on the evaluation-target information acquired and the analytical model, wherein the one or more sample data sets and the evaluation-target information represent information including values of M types (wherein M is an integer having a value independent of N) of parameters based on at least one of N types of feature parameters included in feature-group information about a cell image for use as a sample or an evaluation target, the feature-group information being generated from data of one or more cell images included in a unit, the one or more cell images in the unit being selected from cell images capturing a cell population including a plurality of cells as an imaging subject in accordance with a predetermined requirement, and the feature-group information including values of the N types of feature parameters (wherein N represents an integer having a value of 1 or more) about a morphological feature of a single cell of the cells or a morphological feature of the cell population. Thereby, appropriate cell analysis can be performed per analysis item, analysis approach, and different requirement.

Further, there is no particular limitation for the embodiment of a cell analysis-result outputting apparatus to which the present invention can be applied as long as the apparatus has the following configuration. That is, the aforementioned cell analysis apparatus 1 is an example of the cell analysis-result outputting apparatus.

That is, the cell analysis-result outputting apparatus to which the present invention can be applied includes: an output means (for example, output-information generating unit 48 in FIG. 2) configured to output, as output information, information about an image, the image including a first symbol indicating comparison subject information and a second symbol indicating comparison target information, and the information about the image having a display form changing according to a distance calculated, in a case where information is stored as feature-group information based on data of one or more cell images included in a unit, the one or more cell images in the unit being selected from cell images capturing a cell population including a plurality of cells as an imaging subject in accordance with a predetermined requirement, the information including values of N types of feature parameters (wherein N represents an integer having a value of 1 or more) about a morphological feature of a single cell of the cells or a morphological feature of the cell population, and the comparison subject information including M types (wherein M is an integer having a value independent of N) of parameters is obtained based on at least one of the N types of feature parameters included in the feature-group information of a comparison subject, and the comparison target information including the M types of parameters is calculated based on at least one of the N types of feature parameters included in the feature-group information of a comparison target, and the distance is calculated between the comparison subject information and the comparison target information in terms of a predetermined point of view. Thereby, a user can easily and effectively recognize results from analytical processing on a wide variety of cells, the analytical processing being different in terms of analysis items, analysis approaches, different requirements, and the like.

When a series of processing is performed by software, a program included in the software is installed in a computer and the like via a network and/or storage medium. The computer may be integrated in a dedicated hardware. Further, the computer may be able to perform various functions when various programs are installed, and may be, for example, a general-purpose personal computer.

Example of the storage medium which can contain such a program include not only the removable medium 31 in FIG. 1 which is distributed separately from the apparatus body to provide a user with a program but also a storage medium provided to a user in a state where it is pre-incorporated into the apparatus body. Example of the removable medium 31 includes, for example, a magnetic disk (including a floppy disk), an optical disk, or a magnetic optical disk. Examples of the optical disk include, for example, CD-ROM (Compact Disk-Read Only Memory), DVD (Digital Versatile Disk), and the like. Examples of the magnetic optical disk include MD (Mini-Disk) and the like. Moreover, examples of the storage medium provided to a user in a state where it is pre-incorporated into the apparatus body include, for example, a ROM 112 in FIG. 3, a ROM 212 in FIG. 5, a storage unit 118 in FIG. 2, a hard disk contained in a storage unit 216 in FIG. 5, and the like.

It is noted that steps describing a program stored in a storage medium may be executed in chronological order according to the order of the steps, or may not necessarily be executed in chronological order, or may be executed in parallel or individually.

As described above, the embodiments are merely illustrative, and shall not limit the technical scope of the present invention. The present invention can be implemented in other various embodiments. Further, various modifications such as omission and substitution may be made without departing the spirit of the present invention. These embodiments and variations thereof are included within the range and spirit of the invention described herein or elsewhere, and also included within the range of the invention described in the claims and equivalents thereof.

Below, examples of an apparatus to which the present invention can be applied will be supplementarily described.

[Supplemental Note 11]

A cell-analyzing information generating apparatus, including: a feature-group information generating means configured to generate, as feature-group information, information including values of N types of feature parameters (wherein N represents an integer having a value of 1 or more) about a morphological feature of a single cell of a plurality of cells or a morphological feature of a cell population based on data of one or more cell images included in a unit, the one or more cell images in the unit being selected from cell images capturing the cell population including the cells in accordance with a predetermined requirement; and an information acquiring means configured to acquire, as analyzing information for use in performing predetermined cell analysis, information including values of M types (wherein M is an integer having a value independent of N) of parameters based on at least one of the N types of feature parameters included in the feature-group information.

[Supplemental Note 12]

The cell-analyzing information generating apparatus according to the Supplemental Note 11, wherein the N types of feature parameters includes one or more feature parameters of the cell population in terms of a predetermined point of view, and the information acquiring means is configured to acquire the analyzing information based on one or more feature parameters including at least the one or more feature parameters of the cell population in terms of the predetermined point of view.

[Supplemental Note 13]

The cell-analyzing information generating apparatus according to the Supplemental Note 11 or 12, wherein at least one of the one or more cell images in the unit from which the feature-group information is generated is captured at a different timing, and the analyzing information includes time information capable of specifying a timing of capturing the one or more cell images as one of the values of the M types of parameters.

[Supplemental Note 14]

A method of generating cell-analyzing information which can be performed with a cell-analyzing information generating apparatus configured to generate information for use in performing predetermined cell analysis, the method including: a feature-group information generating step of generating, as feature-group information, information including values of N types of feature parameters (wherein N represents an integer having a value of 1 or more) about a morphological feature of a single cell of a plurality of cells or a morphological feature of a cell population based on data of one or more cell images included in a unit, the one or more cell images in the unit being selected from cell images capturing the cell population including the cells as an imaging subject in accordance with a predetermined requirement; and an information acquiring step of acquiring, as information for use in performing predetermined cell analysis, information including values of M types (wherein M is an integer having a value independent of N) of parameters based on at least one of the N types of feature parameters included in the feature-group information.

[Supplemental Note 15]

A program instructing a computer configured to generate information for use in performing predetermined cell analysis to execute control processing, the control processing including: a feature-group information generating step of generating, as feature-group information, information including values of N types of feature parameters (wherein N represents an integer having a value of 1 or more) about a morphological feature of a single cell of a plurality of cells or a morphological feature of a cell population based on data of one or more cell images included in a unit, the one or more cell images in the unit being selected from cell images capturing the cell population including the cells as an imaging subject in accordance with a predetermined requirement; and an information acquiring step of acquiring, as information for use in performing predetermined cell analysis, information including values of M types (wherein M is an integer having a value independent of N) of parameters based on at least one of the N types of feature parameters included in the feature-group information.

[Supplemental Note 21]

A cell-analysis model generating apparatus, including: an information acquiring means configured to acquire, as one or more sample data sets, information including M types (wherein M is an integer having a value independent of N) of parameter values based on at least one of N types of feature parameters included in feature-group information about a cell image for use as a sample in a case where the feature-group information is retained, the feature-group information being generated from data of one or more cell images included in a unit, the one or more cell images in the unit being selected from cell images capturing a cell population including a plurality of cells as an imaging subject in accordance with a predetermined requirement, and the feature-group information including values of the N types of feature parameters (wherein N represents an integer having a value of 1 or more) about a morphological feature of a single cell of the cells or a morphological feature of the cell population; and a model generating means configured to generate an analytical model for performing cell analysis using the one or more sample data sets acquired.

[Supplemental Note 22]

The cell-analysis model generating apparatus according to the Supplemental Note 21, wherein the N types of feature parameters include one or more feature parameters of the cell population in terms of a predetermined point of view, and the information acquiring means is configured to acquire the one or more sample data sets based on one or more feature parameters including at least the one or more feature parameters of the cell population in terms of the predetermined point of view.

[Supplemental Note 23]

The cell-analysis model generating apparatus according to the Supplemental Note 21 or 22, wherein at least one of the one or more cell images in the unit from which the feature-group information is generated is captured at a different timing, and the one or more sample data sets include time information capable of specifying a timing of capturing the one or more cell images as one of the values of the M types of parameters.

[Supplemental Note 24]

A method of generating a cell analysis model which can be performed with a cell-analysis model generating apparatus configured to generate an analytical model for performing cell analysis, the method including: an information acquiring step of acquiring, as one or more sample data sets, information including values of M types (wherein M is an integer having a value independent of N) of parameters based on at least one of N types of feature parameters included in feature-group information about a cell image for use as a sample in a case where the feature-group information is retained, the feature-group information being generated from data of one or more cell images included in a unit, the one or more cell images in the unit being selected from cell images capturing a cell population including a plurality of cells as an imaging subject in accordance with a predetermined requirement, and the feature-group information including values of the N types of feature parameters (wherein N represents an integer having a value of 1 or more) about a morphological feature of a single cell of the cells or a morphological feature of the cell population; and a model generating step of generating the analytical model using the one or more sample data sets acquired.

[Supplemental Note 25]

A program for instructing a computer configured to generate an analytical model for performing cell analysis to execute control processing, the control processing including: an information acquiring step of acquiring, as one or more sample data sets, information including values of M types (wherein M is an integer having a value independent of N) of parameters based on at least one of N types of feature parameters included in feature-group information about a cell image of a cell population for use as a sample in a case where the feature-group information is retained, the feature-group information being generated from data of one or more cell images included in a unit, the one or more cell images in the unit being selected from cell images capturing a cell population including a plurality of cells as an imaging subject in accordance with a predetermined requirement, and the feature-group information including values of the N types of feature parameters (wherein N represents an integer having a value of 1 or more) about a morphological feature of a single cell of the cells or a morphological feature of the cell population; and a model generating step of generating the analytical model using the one or more sample data sets acquired.

[Supplemental Note 26]

A cell analysis apparatus for performing analytical processing on a cell using an analytical model generated from one or more sample data sets, the apparatus including: an acquisition means configured to acquire data about a cell image to be subjected to analytical evaluation as evaluation-target information, the data being in the same form as the one or more sample data sets; and an analysis means configured to perform analytical processing on the cell image corresponding to the evaluation-target information based on the evaluation-target information acquired and the analytical model, wherein the one or more sample data sets and the evaluation-target information represent information including values of M types (wherein M is an integer having a value independent of N) of parameters based on at least one of N types of feature parameters included in feature-group information about a cell image for use as a sample or an evaluation target, the feature-group information being generated from data of the one or more cell images included in a unit, the one or more cell images in the unit being selected from cell images capturing a cell population including a plurality of cells as an imaging subject in accordance with a predetermined requirement, and the feature-group information including values of the N types of feature parameters (wherein N represents an integer having a value of 1 or more) about a morphological feature of a single cell of the cells or a morphological feature of the cell population.

[Supplemental Note 27]

The cell analysis apparatus according to the Supplemental Note 26, wherein the N types of feature parameters include one or more feature parameters of the cell population in terms of a predetermined point of view, and the one or more sample data sets and the evaluation-target information are information acquired based on one or more feature parameters including at least the one or more feature parameters of the cell population in terms of the predetermined point of view.

[Supplemental Note 28]

The cell-analysis model generating apparatus according to the Supplemental Note 26 or 27, wherein at least one of the one or more cell images in the unit from which the feature-group information is generated is captured at a different timing, and the one or more sample data sets and the evaluation-target information include time information capable of specifying a timing of capturing the one or more cell images as one of the values of the M types of parameters.

[Supplemental Note 291]

A method of cell analysis which can be performed with a cell analysis apparatus configured to conducting analytical processing on a cell using an analytical model generated from one or more sample data set, the method including: an acquisition step of acquiring data about a cell image to be subjected to analytical evaluation as evaluation-target information, the data being in the same form as the one or more sample data sets; and an analysis step of performing analytical processing on the cell image corresponding to the evaluation-target information based on the evaluation-target information acquired and the analytical model, wherein the one or more sample data sets and the evaluation-target information represent information including values of M types (wherein M is an integer having a value independent of N) of parameters based on at least one of N types of feature parameters included in feature-group information about a cell image for use as a sample or an evaluation target, the feature-group information being generated from data of one or more cell images included in a unit, the one or more cell images in the unit being selected from cell images capturing a cell population including a plurality of cells as an imaging subject in accordance with a predetermined requirement, the feature-group information including values of the N types of feature parameters (wherein N represents an integer having a value of 1 or more) about a morphological feature of a single cell of the cells or a morphological feature of the cell population.

[Supplemental Note 292]

A program for instructing a computer configured to control execution of analytical processing on a cell using an analytical model generated from one or more sample data sets to execute the analytical processing, the analytical processing including: an acquisition step of acquiring data about a cell image to be subjected to analytical evaluation as evaluation-target information, the data being in the same form as the one or more sample data sets; and an analysis step of performing analytical processing on the cell image corresponding to the evaluation-target information based on the evaluation-target information acquired and the analytical model, wherein the one or more sample data sets and the evaluation-target information represent information including values of M types (wherein M is an integer having a value independent of N) of parameters based on at least one of N types of feature parameters included in feature-group information about a cell image for use as a sample or an evaluation target, the feature-group information being generated from data of one or more cell images included in a unit, the one or more cell images in the unit being selected from cell images capturing a cell population including a plurality of cells as an imaging subject in accordance with a predetermined requirement, the feature-group information including values of the N types of feature parameters (wherein N represents an integer having a value of 1 or more) about a morphological feature of a single cell of the cells or a morphological feature of the cell population.

Here, problems to be solved by the embodiments of the present invention according to [Supplemental Note 29] to [Supplemental Note 292] above will be described below.

That is, traditionally, the cell staining technology is widely used in the fields of detection of naturally occurring cancers in cancer research, discrimination of heterologous cells from therapeutic cells in regenerative medicine, and clinical studies of mesenchymal stem cells (MSC).

Cells are destroyed when stained by the cell-staining technology as described above. Further, staining reagents are expensive, and cell-staining procedures themselves are troublesome. Accordingly, the present inventors continuously strive to conduct studies to develop an inexpensive and simple technology for non-destructive analysis of cells (see Patent Documents 21 to 25).

[Patent Document 21] Japanese Unexamined Patent Application, Publication No. 2011-232051
[Patent Document 22] Japanese Unexamined Patent Application, Publication No. 2011-229413
[Patent Document 23] Japanese Unexamined Patent Application, Publication No. 2011-229410
[Patent Document 24] Japanese Unexamined Patent Application, Publication No. 2011-229409
[Patent Document 25] Re-publication of PCT International Publication No. 2010/098105

However, depending on cell analysis technologies, items to be analyzed widely vary, and a wide variety of analysis approaches and requirements are available even when the same item is analyzed. For this reason, a distinct analytical model needs to be pre-established for every analysis item, analysis approach, and different requirement. A different analytical model often requires different cell-analyzing information compatible with that model. This means that the structure and type of cell analyzing information are often different when an analytical model is different. As used herein, the term "cell-analyzing information" refers to information about a sample cell required for generating an analytical model, and/or information about a cell to be analyzed. Accordingly, there have demands for efficiently generating cell-analyzing information for each of different analytical models. In other words, there have been demands for efficiently generating compatible cell-analyzing information per analysis item, analysis approach, different requirement, and the like to perform appropriate analysis for each of analysis items, analysis approaches, different requirements, and the like.

The embodiments of the present invention according to [Supplemental Note 29] to [Supplemental Note 292] are made in view of the above circumstances. An object of the present invention is to efficiently generate compatible analytical models per analysis item, analysis approach, different requirement, and the like with regard to cell analysis, and to perform appropriate analysis for each of analysis items, analysis approaches, different requirements, and the like using these analysis models.

[Supplemental Note 31]

A cell analysis-result outputting apparatus including: an output means configured to output, as output information, information about an image, the image including a first symbol indicating comparison subject information and a second symbol indicating comparison target information, and the information about the image having a display form changing according to a distance calculated, in a case where information is stored as feature-group information based on data of one or more cell images included in a unit, the one or more cell images in the unit being selected from cell images capturing a cell population including a plurality of cells as an imaging subject in accordance with a predetermined requirement, the information including values of N types of feature parameters (wherein N represents an integer having a value of 1 or more) about a morphological feature of a single cell of the cells or a morphological feature of the cell population, and the comparison subject information including M types (wherein M is an integer having a value independent of N) of parameters is obtained based on at least one of the N types of feature parameters included in the feature-group information of a comparison subject, and the comparison target information including the M types of parameters is obtained based on at least one of the N types of feature parameters included in the feature-group information of a comparison target, and the distance is calculated between the comparison subject information and the comparison target information in terms of a predetermined point of view.

[Supplemental Note 32]

The cell analysis-result outputting apparatus according to the Supplemental Note 31, wherein the output means is configured to output, as output information, information about the image, the image showing the first symbol and the second symbol arranged at positions, the positions changing according to the distance calculated, within a space defined by S axes (S is an integer having a value equal or less than M) determined based on the M types of parameters.

[Supplemental Note 33]

The cell analysis-result outputting apparatus according to the Supplemental Note 32, wherein the first symbol and the second symbol are points arranged in the space.

[Supplemental Note 34]

The cell analysis-result outputting apparatus according to the Supplemental Note 32, wherein the first symbol and the second symbol are branches arranged in the space.

[Supplemental Note 35]

A method of outputting a result form cell analysis which can be performed with an apparatus configured to output a result of cell analysis, the method including: an output step of outputting, as output information, information about an image, the image including a first symbol indicating comparison subject information and a second symbol indicating comparison target information, and the information about the image having a display form changing according to a distance calculated, in a case where information is stored as feature-group information based on data of one or more cell images included in a unit, the one or more cell images in the unit being selected from cell images capturing a cell population including a plurality of cells as an imaging subject in accordance with a predetermined requirement, the information including values of N types of feature parameters (wherein N represents an integer having a value of 1 or more) about a morphological feature of a single cell of the cells or a morphological feature of the cell population, and the comparison subject information including M types (wherein M is an integer having a value independent of N) of parameters is obtained based on at least one of the N types of feature parameters included in the feature-group information of a comparison subject, and the comparison target information including the M types of parameters is obtained based on at least one of the N types of feature parameters included in the feature-group information of a comparison target, and the distance is calculated between the comparison subject information and the comparison target information in terms of a predetermined point of view.

[Supplemental Note 36]

A program for instructing a computer configured to perform control outputs of a result from cell analysis to execute control processing, the control processing including: an output step of outputting, as output information, information about an image, the image including a first symbol indicating comparison subject information and a second symbol indicating comparison target information, and the information about the image having a display form changing according to a distance calculated, in a case where information is stored as feature-group information based on data of one or more cell images included in a unit, the one or more cell images in the unit being selected from cell images capturing a cell population including a plurality of cells as an imaging subject in accordance with a predetermined requirement, the information including values of N types of feature parameters (wherein N represents an integer having a value of 1 or more) about a morphological feature of a single cell of the cells or a morphological feature of the cell population, and the comparison subject information including M types (wherein M is an integer having a value independent of N) of parameters is obtained based on at least one of the N types of feature parameters included in the feature-group information of a comparison subject, and the comparison target information including the M types of parameters is obtained based on at least one of the N types of feature parameters included in the feature-group information of a comparison target, and the distance is calculated between the comparison subject information and the comparison target information in terms of a predetermined point of view.

Here, problems to be solved by the embodiments of the present invention according to [Supplemental Note 31] to [Supplemental Note 36] above will be described below.

Traditionally, the cell staining technology is widely used in the fields of detection of naturally occurring cancers in cancer research, discrimination of heterologous cells from therapeutic cells in regenerative medicine, and clinical studies of mesenchymal stem cells (MSC).

Cells are destroyed when stained by the cell-staining technology as described above. Further, staining reagents are expensive, and cell-staining procedures themselves are troublesome. Accordingly, the present inventors continuously strive to conduct studies to develop an inexpensive and simple technology for non-destructive analysis of cells (see Patent Documents 31 to 35).

[Patent Document 31] Japanese Unexamined Patent Application, Publication No. 2011-232051
[Patent Document 32] Japanese Unexamined Patent Application, Publication No. 2011-229413
[Patent Document 33] Japanese Unexamined Patent Application, Publication No. 2011-229410
[Patent Document 34] Japanese Unexamined Patent Application, Publication No. 2011-229409
[Patent Document 35] Re-publication of PCT International Publication No. 2010/098105

However, depending on cell analysis technologies, items to be analyzed widely vary, and a wide variety of analysis approaches and requirements are available even when the same item is analyzed. For this reason, a distinct analytical model needs to be pre-established for every analysis item, analysis approach, and different requirement. There have been demands for allowing a user to easily and effectively recognize results from analytical processing on a wide variety of cells, the analytical processing being different in terms of analysis items, analysis approaches, different requirements, and the like as described above.

The embodiments of the present invention according to [Supplemental Note 31] to [Supplemental Note 36] above are made in view of these circumstances. An object of the present invention is to allow a user to easily and effectively recognize results from analytical processing on a wide variety of cells, the analytical processing being different in terms of analysis items, analysis approaches, different requirements, and the like.

EXPLANATION OF REFERENCE NUMERALS

1 . . . Cell analysis apparatus; 11 . . . CPU; 16 . . . Output unit; 18 . . . Storage unit; 31 . . . Removable medium; 41 . . . Cell-image input unit; 42 . . . Feature-group information generating unit; 43 . . . Noise removing unit; 44 . . . Analytical-model generating unit; 45 . . . Evaluation-target information acquiring unit; 46 . . . Evaluation-target information acquiring unit; 47 . . . Analysis unit; 48 . . . output-information generating unit; 61 . . . Feature-group information DB; 62 . . . Cell evaluation DB; 63 . . . Analytical-model retaliation unit; 81 . . . External apparatus; 82 . . . Pre-processing apparatus; 91 . . . Image quantification unit; 92 . . . multiple-image feature-group information generating unit; 93 . . . Heterogeneous information adding unit; 94 . . . Temporal-change information adding unit; 95 . . . Feature-group information output unit 95; 101 . . . Quantified information accumulating unit; 102 . . . First feature-group information accumulating unit; 103 . . . Second feature-group information accumulating unit; 104 . . . Third feature-group information accumulating unit 104

The invention claimed is:
1. An apparatus, comprising:
a central processing unit (CPU) and
a storage unit having stored thereon, a program comprising a set of instructions that, when executed by the CPU, configure the CPU to:
receive one or more first cell images capturing a cell population;
generate, based on the received one or more first cell images, feature-group information, including values of N types of feature parameters, each relating to a feature of a single cell of the cell population or a feature of multiple cells of the cell population, wherein
- N represents an integer having a value of two or more, and
- the N types of feature parameters include at least one first feature parameter relating to a feature of a single cell of the cell population and at least one second feature parameter relating to a feature of multiple cells of the cell population;

determine, based on at least one of the N types of feature parameters, analyzing information including first values of M types of parameters, wherein
- M is an integer having a value of two or more and is independent of N, and
- the M types of parameters include a subset of the N types of feature parameters and a supplementary parameter other than the N types of feature parameters in the feature-group information;

generate an analytical model for predicting cell quality using the analyzing information;

receive one or more second cell images capturing one or more cells to be analyzed;

perform an analysis of the one or more cells to be analyzed using the generated analytical model and second values for the M types of parameters determined based on the one or more second cell images; and generate output information based on a comparison of the first values of the M types of parameters and the second values for the M types of parameters.

2. The apparatus according to claim 1, wherein determining the analyzing information is based on information about a distribution of the at least one second feature parameter relating to a feature of multiple cells of the cell population.

3. The apparatus according to claim 1, wherein
the one or more first cell images includes at least two cell images captured at different time points, and
the analyzing information includes time information specifying a time point of capturing the one or more first cell images as one of the values of the M types of parameters.

4. A method of generating cell information, the method comprising:

receiving one or more first cell images capturing a cell population;

generating, based on the received one or more first cell images, feature-group information including values of N types of feature parameters, each relating to a feature of a single cell of the cell population or a feature of multiple cells of the cell population, wherein
- N represents an integer having a value of two or more, and
- the N types of feature parameters include at least one first feature parameter relating to a feature of a single cell of the cell population and at least one second feature parameter relating to a feature of multiple cells of the cell population;

determining, based on at least one of the N types of feature parameters, analyzing information including first values of M types of parameters, wherein
- M is an integer having a value of two or more and is independent of N, and
- the M types of parameters include a subset of the N types of feature parameters and a supplementary parameter other than the N types of feature parameters in the feature-group information;

generating an analytical model for predicting cell quality using the analyzing information;

receiving one or more second cell images capturing one or more cells to be analyzed;

performing an analysis of one or more cells to be analyzed using the generated analytical model and second values for the M types of parameters determined based on the one or more second cell images; and generating output information based on a comparison of the first values of the M types of parameters and the second values for the M types of parameters.

5. A non-transitory computer readable medium having stored thereon, a plurality of instructions that, when executed by a central processing unit (CPU) configure the CPU to:

receive one or more first cell images capturing a cell population;

generate, based on the received one or more first cell images, feature-group information, including values of N types of feature parameters, each relating to a feature of a single cell of the cell population or a feature of multiple cells of the cell population, wherein
- N represents an integer having a value of two or more, and
- the N types of feature parameters include at least one first feature parameter relating to a feature of a single cell of the cell population and at least one second feature parameter relating to a feature of multiple cells of the cell population;

determine, based on at least one of the N types of feature parameters, analyzing information including first values of M types of parameters, wherein
- M is an integer having a value of two or more and is independent of N, and
- the M types of parameters include a subset of the N types of feature parameters and a supplementary parameter other than the N types of feature parameters in the feature-group information;

generate an analytical model for predicting cell quality using the analyzing information;

receive one or more second cell images capturing one or more cells to be analyzed;

perform an analysis of the one or more cells to be analyzed using the generated analytical model and second values for the M types of parameters determined based on the one or more second cell images; and generate output information based on a comparison of the first values of the M types of parameters and the second values for the M types of parameters.

* * * * *